(12) United States Patent

Parker et al.

(10) Patent No.: US 12,594,427 B2
(45) Date of Patent: Apr. 7, 2026

(54) PROGRAMMING CLOSED-LOOP NEURAL STIMULATION THERAPY

(71) Applicant: Saluda Medical Pty Ltd, Level (AU)

(72) Inventors: Daniel John Parker, Artarmon (AU); James Hamilton Wah, Artarmon (AU); Samuel Nicholas Gilbert, Artarmon (AU); Dean Michael Karantonis, Artarmon (AU); Matthew Marlon Williams, Artarmon (AU); John Louis Parker, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 409 days.

(21) Appl. No.: 18/178,444

(22) Filed: Mar. 3, 2023

(65) Prior Publication Data

US 2023/0277850 A1     Sep. 7, 2023

(30) Foreign Application Priority Data

Mar. 3, 2022     (AU) ................................ 2022900509

(51) Int. Cl.
*A61N 1/36* (2006.01)
*A61N 1/02* (2006.01)
*A61N 1/372* (2006.01)

(52) U.S. Cl.
CPC ......... *A61N 1/36139* (2013.01); *A61N 1/025* (2013.01); *A61N 1/3615* (2013.01); *A61N 1/37252* (2013.01)

(58) Field of Classification Search
None
See application file for complete search history.

(56) References Cited

U.S. PATENT DOCUMENTS 8,406,877 B2 * 3/2013 Smith ................ A61N 1/36139
607/116
9,872,990 B2 * 1/2018 Parker ................ A61N 1/36139
(Continued)

FOREIGN PATENT DOCUMENTS

WO      WO2012155183      11/2012
WO      WO2012155187 A1   11/2012
(Continued)

*Primary Examiner* — Carl H Layno
*Assistant Examiner* — Bryan McAllister Lee
(74) *Attorney, Agent, or Firm* — Barnes & Thornburg LLP

(57) ABSTRACT

A neuromodulation device comprises stimulus electrodes and sense electrodes. A stimulus source provides stimuli to evoke a neural response on a neural pathway. A signal sensed at the sense electrodes includes an evoked neural response. A control unit controls the stimulus source to provide the neural stimulus according to a stimulus intensity parameter; measures an intensity of the evoked response; and completes a feedback loop using the measured intensity and controller parameters to control the stimulus intensity parameter to maintain the measured intensity at a target value. Optimal values of the controller parameters are determined from a representative value of a characteristic of the feedback loop, the representative value having been derived from data of previously programmed patients, and/or the processor is configured to determine optimal values of the one or more controller parameters from a predetermined value of an amplification parameter of the feedback loop.

59 Claims, 13 Drawing Sheets

(56)     References Cited

U.S. PATENT DOCUMENTS

| | | | |
|---|---|---|---|
| 2021/0016091 A1* | 1/2021 | Parker | A61N 1/36139 |
| 2023/0014405 A1 | 1/2023 | Parker et al. | |
| 2023/0149722 A1 | 5/2023 | Schmeling et al. | |
| 2023/0149723 A1 | 5/2023 | Schmeling et al. | |
| 2023/0241397 A1 | 8/2023 | Parker et al. | |

FOREIGN PATENT DOCUMENTS

| | | |
|---|---|---|
| WO | WO2012155188 | 11/2012 |
| WO | WO2015074121 | 5/2015 |
| WO | WO2016090436 A1 | 6/2016 |
| WO | WO2021126587 A1 | 6/2021 |
| WO | WO2021252257 A1 | 12/2021 |
| WO | WO2021252259 A1 | 12/2021 |
| WO | WO2022150638 A1 | 7/2022 |
| WO | WO2022197748 A1 | 9/2022 |
| WO | WO2023035043 A1 | 3/2023 |
| WO | WO2023115132 A1 | 6/2023 |
| WO | WO2023154346 A1 | 8/2023 |

* cited by examiner

600

900

910

Measure patient sensitivity $S$

920

Compute optimal controller gain $K_{opt}$ from $S$ and predetermined trade-off value of loop characteristic

1200 pulsing smooth    1210 spiky    1220

Yes

Low      High

Next

PROGRAMMING CLOSED-LOOP NEURAL STIMULATION THERAPY

The present application claims priority from Australian Provisional Patent Application No 2022900509 filed on 3 Mar. 2022, the contents of which are incorporated herein by reference in their entirety.

TECHNICAL FIELD

The present invention relates to neural stimulation therapy and in particular to selecting patient-appropriate clinical settings for closed-loop neural stimulation therapy.

BACKGROUND OF THE INVENTION

There are a range of situations in which it is desirable to apply neural stimuli in order to alter neural function, a process known as neuromodulation. For example, neuromodulation is used to treat a variety of disorders including chronic neuropathic pain, Parkinson's disease, and migraine. A neuromodulation system applies an electrical pulse (stimulus) to neural tissue (fibres, or neurons) in order to generate a therapeutic effect. In general, the electrical stimulus generated by a neuromodulation system evokes a neural response known as an action potential in a neural fibre which then has either an inhibitory or excitatory effect. Inhibitory effects can be used to modulate an undesired process such as the transmission of pain, or excitatory effects may be used to cause a desired effect such as the contraction of a muscle.

When used to relieve neuropathic pain originating in the trunk and limbs, the electrical pulse is applied to the dorsal column (DC) of the spinal cord, a procedure referred to as spinal cord stimulation (SCS). Such a system typically comprises an implanted electrical pulse generator, and a power source such as a battery that may be transcutaneously rechargeable by wireless means, such as inductive transfer. An electrode array is connected to the pulse generator, and is implanted adjacent the target neural fibre(s) in the spinal cord, typically in the dorsal epidural space above the dorsal column. An electrical pulse of sufficient intensity applied to the target neural fibres by a stimulus electrode causes the depolarisation of neurons in the fibres, which in turn generates an action potential in the fibres. Action potentials propagate along the fibres in orthodromic (towards the head, or rostral) and antidromic (towards the cauda, or caudal) directions. The fibres being stimulated in this way inhibit the transmission of pain from a region of the body innervated by the target neural fibres (the dermatome) to the brain. To sustain the pain relief effects, stimuli are applied repeatedly, for example at a frequency in the range of 30 Hz-100 Hz.

For effective and comfortable neuromodulation, it is necessary to maintain stimulus intensity above a recruitment threshold. Stimuli below the recruitment threshold will fail to recruit sufficient neurons to generate action potentials with a therapeutic effect. In almost all neuromodulation applications, response from a single class of fibre is desired, but the stimulus waveforms employed can evoke action potentials in other classes of fibres which cause unwanted side effects. In pain relief, it is therefore desirable to apply stimuli with intensity below a discomfort threshold, above which uncomfortable or painful percepts arise due to over-recruitment of $A\beta$ fibres. When recruitment is too large, $A\beta$ fibres produce uncomfortable sensations. Stimulation at high intensity may even recruit $A\delta$ fibres, which are sensory nerve fibres associated with acute pain, cold and pressure sensation. It is therefore desirable to maintain stimulus intensity within a therapeutic range between the recruitment threshold and the discomfort threshold.

The task of maintaining appropriate neural recruitment is made more difficult by electrode migration (change in position over time) and/or postural changes of the implant recipient (patient), either of which can significantly alter the neural recruitment arising from a given stimulus, and therefore the therapeutic range. There is room in the epidural space for the electrode array to move, and such array movement from migration or posture change alters the electrode-to-fibre distance and thus the recruitment efficacy of a given stimulus. Moreover, the spinal cord itself can move within the cerebrospinal fluid (CSF) with respect to the dura. During postural changes, the amount of CSF and/or the distance between the spinal cord and the electrode can change significantly. This effect is so large that postural changes alone can cause a previously comfortable and effective stimulus regime to become either ineffectual or painful.

Another control problem facing neuromodulation systems of all types is achieving neural recruitment at a sufficient level for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Attempts have been made to address such problems by way of feedback or closed-loop control, such as using the methods set forth in International Patent Publication No. WO2012/155188 by the present applicant. Feedback control seeks to compensate for relative nerve/electrode movement by controlling the intensity of the delivered stimuli so as to maintain a substantially constant neural recruitment. The intensity of a neural response evoked by a stimulus may be used as a feedback variable representative of the amount of neural recruitment. A signal representative of the neural response may be sensed by a measurement electrode in electrical communication with the recruited neural fibres, and processed to obtain the feedback variable. Based on the response intensity, the intensity of the applied stimulus may be adjusted to maintain the response intensity within a therapeutic range.

It is therefore desirable to accurately measure the intensity and other characteristics of a neural response evoked by the stimulus. The action potentials generated by the depolarisation of a large number of fibres by a stimulus sum to form a measurable signal known as an evoked compound action potential (ECAP). Accordingly, an ECAP is the sum of responses from a large number of single fibre action potentials. The ECAP generated from the depolarisation of a group of similar fibres may be measured at a measurement electrode as a positive peak potential, then a negative peak, followed by a second positive peak. This morphology is caused by the region of activation passing the measurement electrode as the action potentials propagate along the individual fibres.

Approaches proposed for obtaining a neural response measurement are described by the present applicant in International Patent Publication No. WO2012/155183, the content of which is incorporated herein by reference.

However, neural response measurement can be a difficult task as a neural response component in the sensed signal will typically have a maximum amplitude in the range of microvolts. In contrast, a stimulus applied to evoke the response is typically several volts, and manifests in the measured response as crosstalk of that magnitude. Moreover, stimulus generally results in electrode artefact, which manifests in the measured response as a decaying output of the order of several millivolts after the end of the stimulus. As the neural response can be contemporaneous with the stimulus crosstalk and/or the stimulus artefact, neural response measurements present a difficult challenge of measurement amplifier design. For example, to resolve a 10 μV ECAP with 1 μV resolution in the presence of stimulus crosstalk of 5 V requires an amplifier with a dynamic range of 134 dB, which is impractical in implantable devices. In practice, many non-ideal aspects of a circuit lead to artefact, and as these aspects mostly result a time-decaying artefact waveform of positive or negative polarity, their identification and elimination can be laborious.

Evoked neural responses are less difficult to detect when they appear later in time than the artefact, or when the signal-to-noise ratio is sufficiently high. The artefact is often restricted to a time of 1-2 ms after the stimulus and so, provided the neural response is detected after this time window, a neural response measurement can be more easily obtained. This is the case in surgical monitoring where there are large distances (e.g. more than 12 cm for nerves conducting at 60 ms$^{-1}$) between the stimulus and measurement electrodes so that the propagation time from the stimulus site to the measurement electrodes exceeds 2 ms, which is longer than the typical duration of stimulus artefact.

However, to characterize the responses from the dorsal column, high stimulation currents are required. Similarly, any implanted neuromodulation device will necessarily be of compact size, so that for such devices to monitor the effect of applied stimuli, the stimulus electrode(s) and measurement electrode(s) will necessarily be in close proximity. In such situations the measurement process must overcome artefact directly.

Closed-loop neural stimulation therapy is governed by a number of parameters to which values must be assigned to implement the therapy. The effectiveness of the therapy depends in large measure on the suitability of the assigned parameter values to the patient undergoing the therapy. As patients vary significantly in their physiological characteristics, a "one-size-fits-all" approach to parameter value assignment is likely to result in ineffective therapy for a large proportion of patients: An important preliminary task, once a neuromodulation device has been implanted in a patient, is therefore to assign values to the therapy parameters that maximise the effectiveness of the therapy the device will deliver to that particular patient. This task is known as programming or fitting the device. Programming generally involves applying certain test stimuli via the device, recording responses, and based on the recorded responses, inferring or calculating the most effective parameter values for the patient. The resulting parameter values are then formed into a "program" that may be loaded to the device to govern subsequent therapy. Some of the recorded responses may be neural responses evoked by the test stimuli, which provide an objective source of information that may be analysed along with subjective responses elicited from the patient. In an effective programming system, the more responses that are analysed, the more suitable the eventual assigned parameter values should be for the patient.

However, programming may be costly and time-consuming if unnecessarily prolonged. There is therefore an incentive to minimise the number of test stimuli to be applied and the amount of information to be recorded and analysed in order to produce the assigned values of the therapy parameters. One task of particular importance in programming a closed-loop neural stimulation therapy is to set a gain for the closed-loop controller. International Patent Publication no. WO2016/090436 by the present applicant, the content of which is herein incorporated by reference, describes how increasing controller gain in an integral feedback controller reduces the component of variation in the stimulus intensity due to periodic postural variations (referred to herein as a posture wave) such as heartbeat. International Patent Publication no. WO2016/090436 also describes how increasing controller gain increases the noise in the stimulus intensity due to amplifier noise and other noise sources. Setting the appropriate controller gain is therefore a matter of trading off posture wave attenuation with noise attenuation. International Patent Publication no. WO2016/090436 also describes how this may be done by choosing an arbitrary cutoff frequency for the loop that is thought to be an acceptable trade-off point for the bulk of patients, and computing the controller gain from the measured patient sensitivity so as to achieve such a cutoff frequency. However, using an arbitrary cutoff frequency as disclosed in WO2016/090436 may not produce a suitable controller gain for every patient, or even for the bulk of patients.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood to mean that the element may be any one of the listed options, or may be any combination of two or more of the listed options.

SUMMARY OF THE INVENTION

Disclosed herein are methods and systems for programming closed-loop neurostimulation therapy that result in controller gains that are more suitable for each particular patient than previously achievable. The methods and systems according to some aspects of the present technology are informed by data on the preferences of previous patients who have been successfully programmed by manual methods. Such methods and systems utilise this data to identify a generally acceptable trade-off point from which a suitable controller gain may be obtained for a particular patient, given certain measurements from the patient. The trade-off point may be achieved by computation as a function of controller gain or by measurement as controller gain is varied. The trade-off point may be expressed as a value of a loop characteristic such as loop gain, loop cutoff frequency, loop response time constant, noise amplification, posture wave amplification, or total amplification.

The methods and systems according to other aspects of the present technology use qualitative feedback about the patient's sensations to inform the choice of controller gain. The disclosed aspects use such qualitative feedback to vary the controller gain in an intelligent manner to efficiently reach a trade-off point that is acceptable for the patient.

According to a first aspect of the present technology, there is provided a neuromodulation system comprising a neuromodulation device for controllably delivering a neural stimulus, and a processor. The neuromodulation device comprises: a plurality of implantable electrodes including one or more stimulus electrodes and one or more sense electrodes; a stimulus source configured to provide a neural stimulus to be delivered via the one or more stimulus electrodes to a neural pathway of a patient in order to evoke a neural response on the neural pathway; measurement circuitry configured to process a signal sensed at the one or more sense electrodes, the sensed signal including an evoked neural response; and a control unit configured to: control the stimulus source to provide the neural stimulus according to a stimulus intensity parameter; measure an intensity of the evoked neural response in the sensed signal; and implement a feedback controller which completes a feedback loop, the feedback controller configured to use the measured intensity and one or more controller parameters to control the stimulus intensity parameter so as to maintain the measured intensity at a target value. The processor is configured to determine optimal values of the one or more controller parameters from a representative value of a characteristic of the feedback loop, the representative value having been derived from data of previously programmed patients.

According to a second aspect of the present technology, there is provided an automated method of controlling a neuromodulation device to deliver a neural stimulus to neural tissue of a patient. The method comprises: delivering the neural stimulus to the neural tissue according to a value of a stimulus intensity parameter; measuring an intensity of a neural response evoked by the stimulus, completing a feedback loop by using the measured intensity and one or more controller parameters to control the stimulus intensity parameter so as to maintain the measured intensity at a target value; and determining optimal values of the one or more controller parameters from a representative value of a characteristic of the feedback loop, the representative value having been derived from data of previously programmed patients.

In some embodiments of the first and/or second aspects of the present technology, a sensitivity of the neural pathway may be measured based on the values of the stimulus intensity parameter and the corresponding measured neural response intensities. The one or more controller parameters may comprise a controller gain, and the optimal value of the controller gain may be determined using the measured sensitivity as well as the representative value of the loop characteristic. The representative value of the loop characteristic may be a loop gain, and the optimal value of the controller gain may be determined by dividing the loop gain by the measured sensitivity. The optimal value of the controller gain may be determined by: determining an optimal value of loop gain of the feedback loop from the representative value of the loop characteristic, and dividing the optimal value of the loop gain by the measured sensitivity. The representative value of the loop characteristic may be a cutoff frequency of the feedback loop, a time constant of the feedback loop, a noise amplification ratio of the feedback loop, a posture wave amplification ratio of the feedback loop, and/or a total amplification of the feedback loop, the total amplification comprising a noise amplification ratio of the feedback loop and a posture wave amplification ratio of the feedback loop. Some embodiments may further comprise an external sensor configured to measure a frequency of the posture wave.

In some embodiments of the first and/or second aspects of the present technology, the one or more controller parameters comprises a controller gain, and the optimal value of the controller gain is determined by: determining a value of the loop characteristic; adjusting the controller gain based on the determined value and the representative value of the loop characteristic; and repeating the measuring and adjusting until the determined value of the loop characteristic is within a predetermined distance from the representative value of the loop characteristic. The value of the loop characteristic may be determined by measuring a loop gain of the feedback loop from a response of the neural response intensity to a step change in the target value. The representative value of the loop characteristic may be the loop gain of the feedback loop, and the measured value of the loop characteristic may be the measured loop gain. The representative value of the loop characteristic may be a cutoff frequency of the feedback loop, and the value of the loop characteristic may be determined from the measured loop gain. The representative value of the loop characteristic may be a time constant of the feedback loop, and the value of the loop characteristic may be determined from the measured loop gain. The representative value of the loop characteristic may be a noise amplification ratio of the feedback loop, and the value of the loop characteristic may be determined from the measured loop gain. The representative value of the loop characteristic may be a posture wave amplification ratio of the feedback loop, and the value of the loop characteristic may be determined from the measured loop gain. The representative value of the loop characteristic may be a total amplification of the feedback loop, the total amplification comprising a noise amplification ratio of the feedback loop and a posture wave amplification ratio of the feedback loop, and the value of the loop characteristic may be determined from the measured loop gain. An external sensor may be used to measure a frequency of the posture wave.

Some embodiments may further comprise an external computing device in communication with the neuromodulation device. The processor may form part of the external computing device. The processor may form part of the neuromodulation device.

Some embodiments may further comprise measuring a sensitivity of the neural tissue based on the values of the stimulus intensity parameter and the corresponding measured neural response intensities. The one or more controller parameters may comprise a controller gain, and determining the optimal value of the controller gain may use the measured sensitivity as well as the representative value of the loop characteristic.

In some embodiments, the one or more controller parameters may comprise a controller gain, and determining the optimal value of the controller gain may comprise: measuring a value of the loop characteristic; adjusting the controller gain based on the measured value and the representative value of the loop characteristic; and repeating the measuring and adjusting until the measured value of the loop characteristic is within a predetermined distance from the representative value of the loop characteristic. Measuring the value of the loop characteristic may comprise measuring a loop gain of the feedback loop from a response of the neural response intensity to a step change in the target value.

According to a third aspect of the present technology, there is provided a neural stimulation system comprising a neuromodulation device for controllably delivering a neural stimulus, and a processor. The neuromodulation device comprises a plurality of implantable electrodes including one or more stimulus electrodes and one or more sense electrodes; a stimulus source configured to provide a neural stimulus to be delivered via the one or more stimulus electrodes to a neural pathway of a patient in order to evoke a neural response on the neural pathway; measurement circuitry configured to process a signal sensed at the one or more sense electrodes subsequent to the delivered neural stimulus, the sensed signal including an evoked neural response; and a control unit configured to: control the stimulus source to provide the neural stimulus according to a stimulus intensity parameter; measure an intensity of the evoked neural response in the sensed signal; and implement a feedback controller which completes a feedback loop, the feedback controller configured to use the measured intensity and one or more controller parameters to control the stimulus intensity parameter so as to maintain the measured intensity at a target value. The processor is configured to determine optimal values of the one or more controller parameters from a predetermined value of an amplification parameter of the feedback loop.

According to a fourth aspect of the present technology, there is provided an automated method of controlling a neuromodulation device to deliver a neural stimulus to neural tissue of a patient. The method comprises delivering the neural stimulus to the neural tissue according to a stimulus intensity parameter; measuring an intensity of a neural response evoked by the stimulus, completing a feedback loop by using the measured intensity and one or more controller parameters to control the stimulus intensity parameter so as to maintain the measured intensity at a target value; and determining optimal values of the one or more controller parameters from a predetermined value of an amplification parameter of the feedback loop.

In some embodiments of the third and/or fourth aspects of the present technology, a sensitivity of the neural pathway may be measured based on the values of the stimulus intensity parameter and the corresponding measured neural response intensities. The one or more controller parameters may comprise a controller gain, and the optimal value of the controller gain may be determined using the measured sensitivity as well as the predetermined value of the amplification parameter of the feedback loop. The optimal value of the controller gain may be determined by: determining an optimal value of loop gain of the feedback loop from the predetermined value, and dividing the optimal value of the loop gain by the measured sensitivity. The predetermined value may be a noise amplification ratio of the feedback loop, a posture wave amplification ratio of the feedback loop, or a total amplification of the feedback loop, the total amplification comprising a noise amplification ratio of the feedback loop and a posture wave amplification ratio of the feedback loop. An external sensor may be used to measure a frequency of the posture wave.

In some embodiments of the third and/or fourth aspects of the present technology, the one or more controller parameters may comprise a controller gain, and the optimal value of the controller gain may be determined by: determining a value of the amplification parameter; adjusting the controller gain based on the determined value and the predetermined value of the amplification parameter; and repeating the measuring and adjusting until the determined value of the amplification parameter is within a predetermined distance from the predetermined value of the amplification parameter. The value of the amplification parameter may be determined by measuring a loop gain of the feedback loop from a response of the neural response intensity to a step change in the target value. The predetermined value of the amplification parameter may be a noise amplification ratio of the feedback loop, and the value of the amplification parameter may be determined from the measured loop gain. The predetermined value of the amplification parameter may be a posture wave amplification ratio of the feedback loop, and the value of the amplification parameter may be determined from the measured loop gain. The predetermined value of the amplification parameter may be a total amplification of the feedback loop, the total amplification comprising a noise amplification ratio of the feedback loop and a posture wave amplification ratio of the feedback loop, and the value of the amplification parameter may be determined from the measured loop gain.

Some embodiments may further comprise an external computing device in communication with the neuromodulation device. The processor may form part of the external computing device. The processor may form part of the neuromodulation device.

According to a fifth aspect of the present technology, there is provided a closed-loop neuromodulation system comprising: a closed-loop neuromodulation device, and a processor. The closed-loop neuromodulation device comprises a feedback controller which completes a feedback loop, the feedback controller using one or more controller parameters to control a stimulus parameter so as to maintain a measured neural response intensity at a target. The processor is configured to compute an optimal value of the one or more controller parameters of the feedback loop of the closed-loop neurostimulation device from a representative value of a characteristic of the feedback loop, the representative value having been derived from data of previously programmed patients.

According to a sixth aspect of the present technology, there is provided a closed-loop neuromodulation system comprising an implantable closed-loop neuromodulation device and an external computing device in communication with the closed-loop neuromodulation device. The implantable closed-loop neuromodulation device comprises a feedback controller which completes a feedback loop, the feedback controller using a controller gain to control a stimulus parameter so as to maintain a measured neural response intensity at a target; and an external computing device in communication with the closed-loop neuromodulation device. The external computing device comprises a display, and a processor configured to: render one or more controls on the display; adjust, dependent on activation of one of the one or more controls by a user, a value of a controller gain of the feedback loop of the closed loop neuromodulation device; and repeat the adjusting until a satisfactory controller gain is achieved.

According to a seventh aspect of the present technology, there is provided an automated method of controlling a closed-loop neuromodulation device to deliver a neural stimulus to a patient using an external computing device in communication with the neuromodulation device. The method comprises: rendering, by a processor of the external computing device, one or more controls on a display of the external computing device; adjusting, dependent on activation of one of the one or more controls by a user, a value of a controller gain of the feedback loop of the closed-loop neuromodulation device; and repeating the adjusting until a satisfactory controller gain is achieved.

References herein to estimation, determination, comparison and the like are to be understood as referring to an automated process carried out on data by a processor operating to execute a predefined procedure suitable to effect the described estimation, determination and/or comparison step(s). The technology disclosed herein may be implemented in hardware (e.g., using digital signal processors, application specific integrated circuits (ASICs) or field programmable gate arrays (FPGAs)), or in software (e.g., using instructions tangibly stored on non-transitory computer-readable media for causing a data processing system to perform the steps described herein), or in a combination of hardware and software. The disclosed technology can also be embodied as computer-readable code on a computer-readable medium. The computer-readable medium can include any data storage device that can store data which can thereafter be read by a computer system. Examples of the computer-readable medium include read-only memory ("ROM"), random-access memory ("RAM"), magnetic tape, optical data storage devices, flash storage devices, or any other suitable storage devices. The computer-readable medium can also be distributed over network-coupled computer systems so that the computer-readable code is stored and/or executed in a distributed fashion.

BRIEF DESCRIPTION OF THE DRAWINGS

One or more implementations of the invention will now be described with reference to the accompanying drawings, in which:

FIGS. 12a to 12d illustrate examples of user interfaces presented to a patient in accordance with respective implementations of an aspect of the present technology.

DETAILED DESCRIPTION OF THE PRESENT TECHNOLOGY

Figure 1:
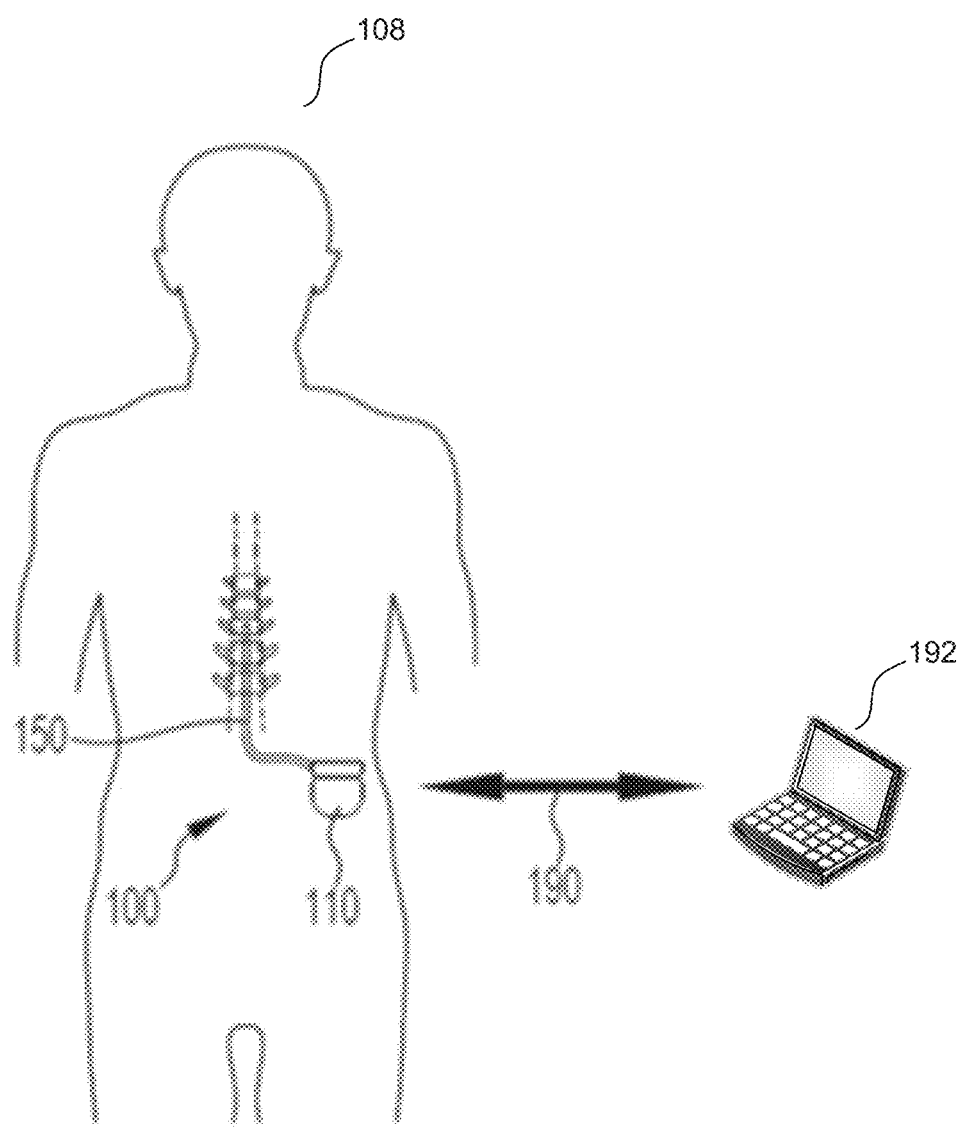
FIG. 1 schematically illustrates an implanted spinal cord stimulator, according to one implementation of the present technology.

FIG. 1 schematically illustrates an implanted spinal cord stimulator 100 in a patient 108, according to one implementation of the present technology. Stimulator 100 comprises an electronics module 110 implanted at a suitable location. In one implementation, stimulator 100 is implanted in the patient's lower abdominal area or posterior superior gluteal region. In other implementations, the electronics module 110 is implanted in other locations, such as in a flank or sub-clavicularly. Stimulator 100 further comprises an electrode array 150 implanted within the epidural space and connected to the module 110 by a suitable lead. The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for stimulation and measurement. The electrodes may pierce or affix directly to the tissue itself.

Numerous aspects of the operation of implanted stimulator 100 may be programmable by an external computing device 192, which may be operable by a user such as a clinician or the patient 108. Moreover, implanted stimulator 100 serves a data gathering role, with gathered data being communicated to external device 192 via a transcutaneous communications channel 190. Communications channel 190 may be active on a substantially continuous basis, at periodic intervals, at non-periodic intervals, or upon request from the external device 192. External device 192 may thus provide a clinical interface configured to program the implanted stimulator 100 and recover data stored on the implanted stimulator 100. This configuration is achieved by program instructions collectively referred to as the Clinical Programming Application (CPA) and stored in ai instruction memory of the clinical interface.

Figure 2:
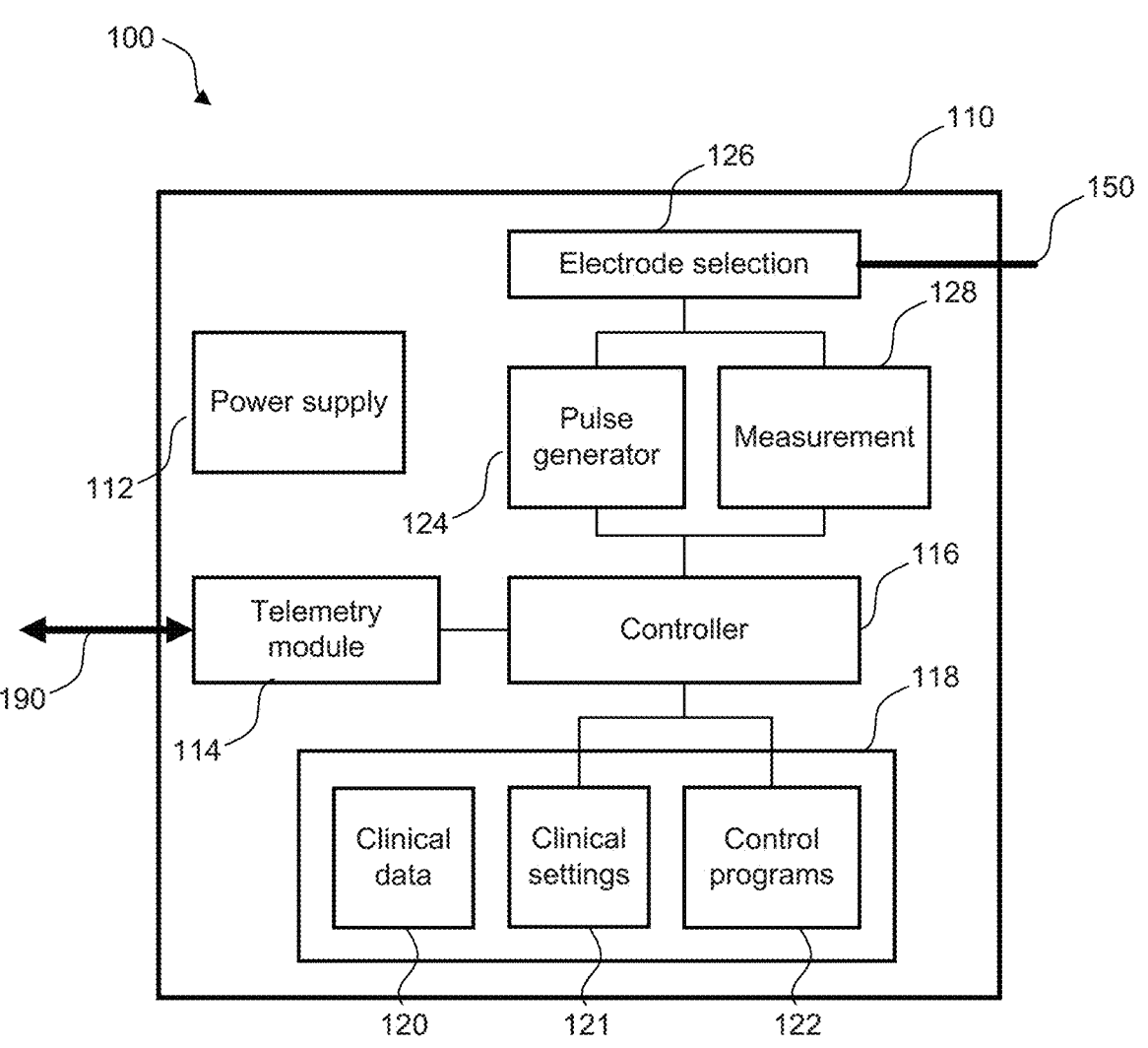
FIG. 2 is a block diagram of the stimulator of FIG. 1.

FIG. 2 is a block diagram of the stimulator 100. Electronics module 110 contains a battery 112 and a telemetry module 114. In implementations of the present technology, any suitable type of transcutaneous communications channel 190, such as infrared (IR), radiofrequency (RF), capacitive and/or inductive transfer, may be used by telemetry module 114 to transfer power and/or data to and from the electronics module 110 via communications channel 190. Module controller 116 has an associated memory 118 storing one or more of clinical data 120, clinical settings 121, control programs 122, and the like. Controller 116 controls a pulse generator 124 to generate stimuli, such as in the form of electrical pulses, in accordance with the clinical settings 121 and control programs 122. Electrode selection module 126 switches the generated pulses to the selected electrode(s) of electrode array 150, for delivery of the pulses to the tissue surrounding the selected electrode(s). Measurement circuitry 128, which may comprise an amplifier and/or an analog-to-digital converter (ADC), is configured to process signals comprising neural responses sensed at measurement electrode(s) of the electrode array 150 as selected by electrode selection module 126.

Figure 3:
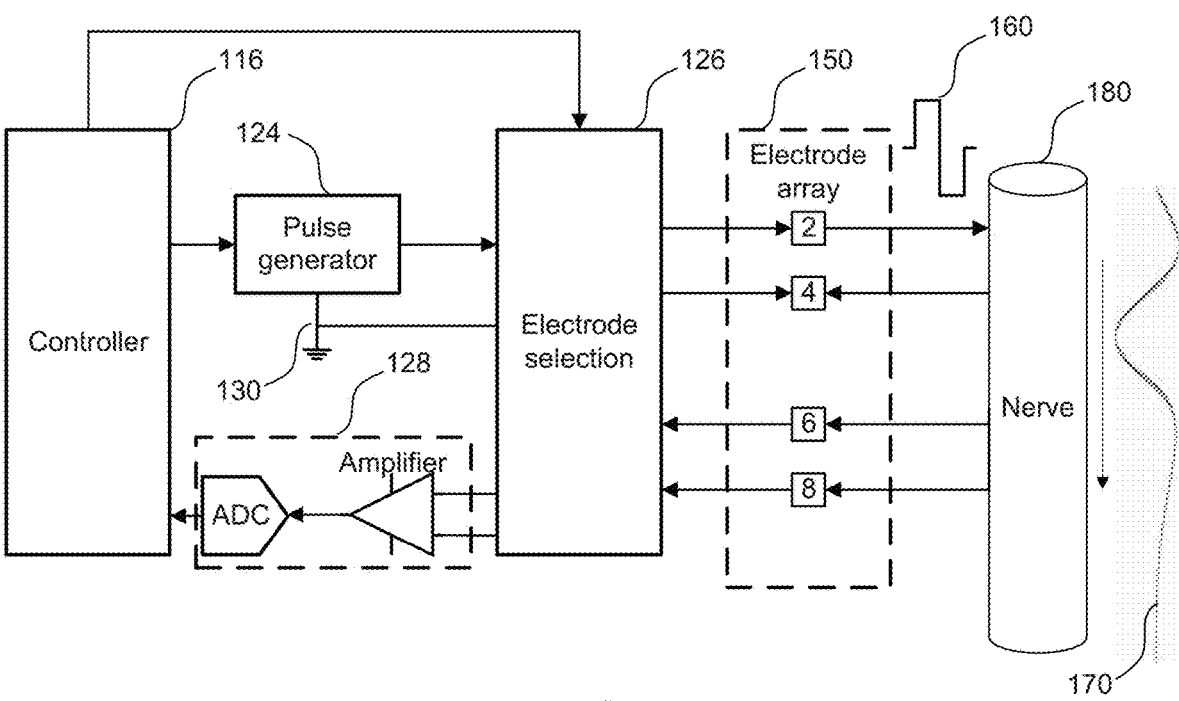
FIG. 3 is a schematic illustrating interaction of the implanted stimulator of FIG. 1 with a nerve.

FIG. 3 is a schematic illustrating interaction of the implanted stimulator 100 with a nerve 180 in the patient 108. In the implementation illustrated in FIG. 3 the nerve 180 may be located in the spinal cord, however in alternative implementations the stimulator 100 may be positioned adjacent any desired neural tissue including a peripheral nerve, visceral nerve, parasympathetic nerve or a brain structure. Electrode selection module 126 selects a stimulus electrode 2 of electrode array 150 through which to deliver a pulse from the pulse generator 124 to surrounding tissue including nerve 180. A pulse may comprise one or more phases, e.g., a biphasic stimulus pulse 160 comprises two phases. Electrode selection module 126 also selects a return electrode 4 of the electrode array 150 for stimulus current return in each phase, to maintain a zero net charge transfer. An electrode may act as both a stimulus and a return electrode over a complete multiphasic stimulus pulse. The use of two electrodes in this manner for delivering and returning current in each stimulus phase is referred to as bipolar stimulation. Alternative embodiments may apply other forms of bipolar stimulation, or may use a greater number of stimulus and/or return electrodes. The set of stimulus and return electrodes is referred to as the stimulus electrode configuration. Electrode selection module 126 is illustrated as connecting to a ground 130 of the pulse generator 124 to enable stimulus current return via the return electrode 4. However, other connections for charge recovery may be used in other implementations.

Delivery of an appropriate stimulus via electrodes 2 and 4 to the nerve 180 evokes a neural response 170 comprising an evoked compound action potential (ECAP) which will propagate along the nerve 180 as illustrated at a rate known as the conduction velocity. The ECAP may be evoked for therapeutic purposes, which in the case of a spinal cord stimulator for chronic pain may be to create paraesthesia at a desired location. To this end, the stimulus electrodes 2 and 4 are used to deliver stimuli periodically at any therapeutically suitable frequency, for example 30 Hz, although other frequencies may be used including frequencies as high as the kHz range. In alternative implementations, stimuli may be delivered in a non-periodic manner such as in bursts, or sporadically, as appropriate for the patient 108. To program the stimulator 100 to the patient 108, a clinician may cause the stimulator 100 to deliver stimuli of various configurations which seek to produce a sensation that is experienced by the user as paraesthesia. When a stimulus electrode configuration is found which evokes paraesthesia in a location and of a size which is congruent with the area of the patient's body affected by pain and of a quality that is comfortable for the patient, the clinician or the patient nominates that configuration for ongoing use. The therapy parameters may be loaded into the memory 118 of the stimulator 100 as the clinical settings 121.

Figure 6:
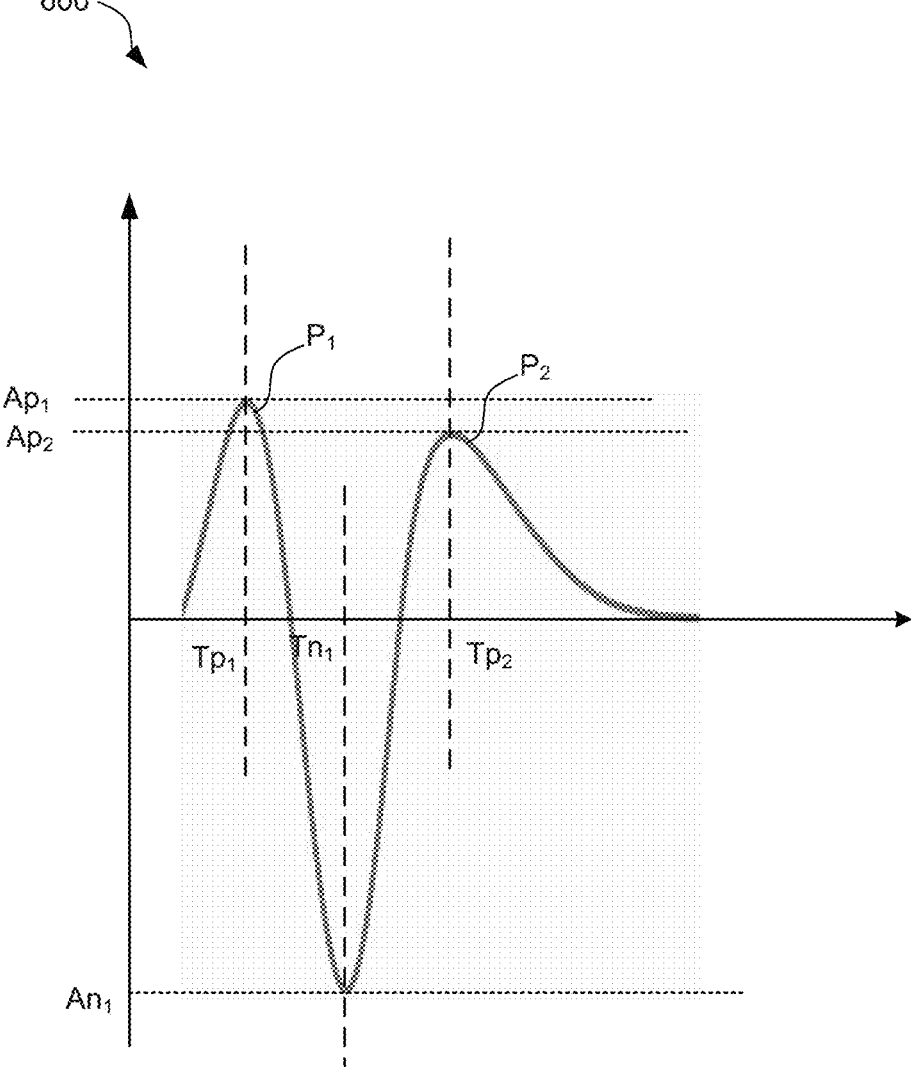
FIG. 6 illustrates the typical form of an electrically evoked compound action potential (ECAP) of a healthy subject.

FIG. 6 illustrates the typical form of an ECAP 600 of a healthy subject, as recorded at a single measurement electrode referenced to the system ground 130. The shape and duration of the single-ended ECAP 600 shown in FIG. 6 is predictable because it is a result of the ion currents produced by the ensemble of fibres depolarising and generating action potentials (APs) in response to stimulation. The evoked action potentials (EAPs) generated synchronously among a large number of fibres sum to form the ECAP 600. The ECAP 600 generated from the synchronous depolarisation of a group of similar fibres comprises a positive peak P1, then a negative peak N1, followed by a second positive peak P2. This shape is caused by the region of activation passing the measurement electrode as the action potentials propagate along the individual fibres.

The ECAP may be recorded differentially using two measurement electrodes, as illustrated in FIG. 3. Depending on the polarity of recording, a differential ECAP may take an inverse form to that shown in FIG. 6, i.e. a form having two negative peaks N1 and N2, and one positive peak P1. Alternatively, depending on the distance between the two measurement electrodes, a differential ECAP may resemble the time derivative of the ECAP 600, or more generally the difference between the ECAP 600 and a time-delayed copy thereof.

The ECAP 600 may be characterised by any suitable characteristic(s) of which some are indicated in FIG. 6. The amplitude of the positive peak P1 is $Ap_1$ and occurs at time $Tp_1$. The amplitude of the positive peak P2 is $Ap_2$ and occurs at time $Tp_2$. The amplitude of the negative peak P1 is $An_1$ and occurs at time $Tn_1$. The peak-to-peak amplitude is $Ap_1+An_1$. A recorded ECAP will typically have a maximum peak-to-peak amplitude in the range of microvolts and a duration of 2 to 3 ms.

The stimulator 100 is further configured to detect the existence and measure the intensity of ECAPs 170 propagating along nerve 180, whether such ECAPs are evoked by the stimulus from electrodes 2 and 4, or otherwise evoked. To this end, any electrodes of the array 150 may be selected by the electrode selection module 126 to serve as recording electrode 6 and reference electrode 8, whereby the electrode selection module 126 selectively connects the chosen electrodes to the inputs of the measurement circuitry 128. Thus, signals sensed by the measurement electrodes 6 and 8 subsequent to the respective stimuli are passed to the measurement circuitry 128, which may comprise a differential amplifier and an analog-to-digital converter (ADC), as illustrated in FIG. 3. The measurement circuitry 128 for example may operate in accordance with the teachings of the above-mentioned International Patent Publication No. WO2012/155183.

Signals sensed by the measurement electrodes 6, 8 and processed by measurement circuitry 128 are further processed by an ECAP detector implemented within controller 116, configured by control programs 122, to obtain information regarding the effect of the applied stimulus upon the nerve 180. In some implementations, the sensed signals are processed by the ECAP detector in a manner which measures and stores one or more characteristics from each evoked neural response or group of evoked neural responses contained in the sensed signal. In one such implementation, the characteristics comprise a peak-to-peak ECAP amplitude in microvolts (μV). For example, the sensed signals may be processed by the ECAP detector to determine the peak-to-peak ECAP amplitude in accordance with the teachings of International Patent Publication No. WO2015/074121, the contents of which are incorporated herein by reference. Alternative implementations of the ECAP detector may measure and store an alternative characteristic from the neural response, or may measure and store two or more characteristics from the neural response.

Stimulator 100 applies stimuli over a potentially long period such as days, weeks, or months and during this time may store characteristics of neural responses, clinical settings, paraesthesia target level, and other operational parameters in memory 118. To effect suitable SCS therapy, stimulator 100 may deliver tens, hundreds or even thousands of stimuli per second, for many hours each day. Each neural response or group of responses generates one or more characteristics such as a measure of the intensity of the neural response. Stimulator 100 thus may produce such data at a rate of tens or hundreds of Hz, or even kHz, and over the course of hours or days this process results in large amounts of clinical data 120 which may be stored in the memory 118. Memory 118 is however necessarily of limited capacity and care is thus required to select compact data forms for storage into the memory 118, to ensure that the memory 118 is not exhausted before such time that the data is expected to be retrieved wirelessly by external device 192, which may occur only once or twice a day, or less.

Figure 4A:
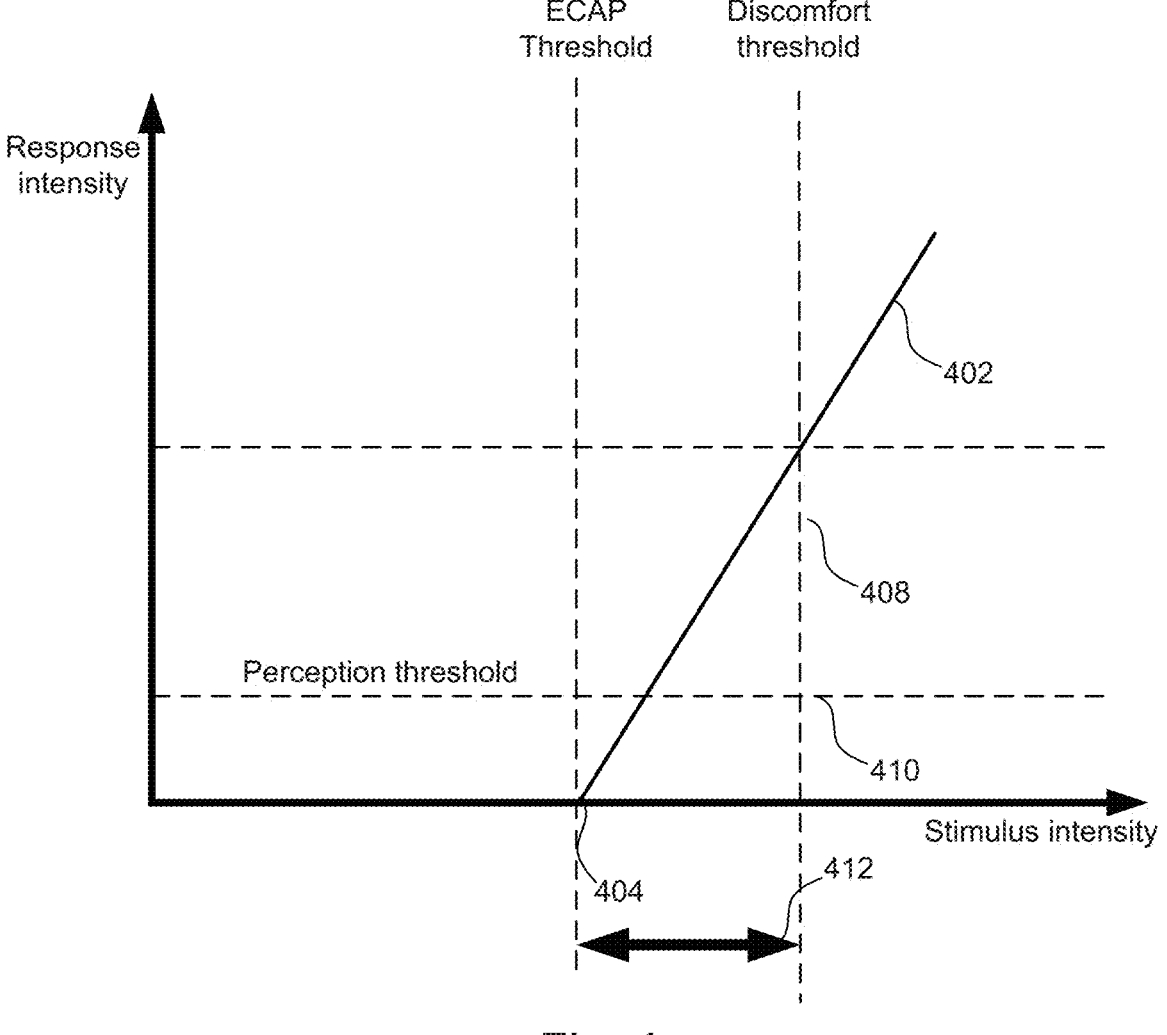
FIG. 4a illustrates an idealised activation plot for one posture of a patient undergoing neurostimulation.

An activation plot, or growth curve, is an approximation to the relationship between stimulus intensity (e.g. an amplitude of the current pulse 160) and intensity of neural response 170 resulting from the stimulus (e.g. an ECAP amplitude). FIG. 4*a* illustrates an idealised activation plot 402 for one posture of the patient 108. The activation plot 402 shows a linearly increasing ECAP amplitude for stimulus intensity values above a threshold 404 referred to as the ECAP threshold. The ECAP threshold exists because of the binary nature of fibre recruitment; if the field strength is too low, no fibres will be recruited. However, once the field strength exceeds a threshold, fibres begin to be recruited, and their individual evoked action potentials are independent of the strength of the field. The ECAP threshold 404 therefore reflects the field strength at which significant numbers of fibres begin to be recruited, and the increase in response intensity with stimulus intensity above the ECAP threshold reflects increasing numbers of fibres being recruited. Below the ECAP threshold 404, the ECAP amplitude may be taken to be zero. Above the ECAP threshold 404, the activation plot 402 has a positive, approximately constant slope indicating a linear relationship between stimulus intensity and the ECAP amplitude. Such a relationship may be modelled as:

$$y = \begin{cases} S(s - T), & s \geq T \\ 0, & s < T \end{cases} \qquad (1)$$

where s is the stimulus intensity, y is the ECAP amplitude, T is the ECAP threshold and S is the slope of the activation plot (referred to herein as the patient sensitivity). The slope S and the ECAP threshold T are the key parameters of the activation plot 402.

FIG. 4a also illustrates a discomfort threshold 408, which is a stimulus intensity above which the patient 108 experiences uncomfortable or painful stimulation. FIG. 4a also illustrates a perception threshold 410. The perception threshold 410 corresponds to an ECAP amplitude that is perceivable by the patient. There are a number of factors which can influence the position of the perception threshold 410, including the posture of the patient. Perception threshold 410 may correspond to a stimulus intensity that is greater than the ECAP threshold 404, as illustrated in FIG. 4a, if patient 108 does not perceive low levels of neural activation. Conversely, the perception threshold 410 may correspond to a stimulus intensity that is less than the ECAP threshold 404, if the patient has a high perception sensitivity to lower levels of neural activation than can be detected in an ECAP, or if the signal to noise ratio of the ECAP is low.

For effective and comfortable operation of an implantable neuromodulation device such as the stimulator 100, it is desirable to maintain stimulus intensity within a therapeutic range 412. A stimulus intensity within a therapeutic range 412 is above the ECAP threshold 404 and below the discomfort threshold 408. In principle, it would be straightforward to measure these limits and ensure that stimulus intensity, which may be closely controlled, always falls within the therapeutic range 412. However, the activation plot, and therefore the therapeutic range 412, varies with the posture of the patient 108.

Figure 4B:
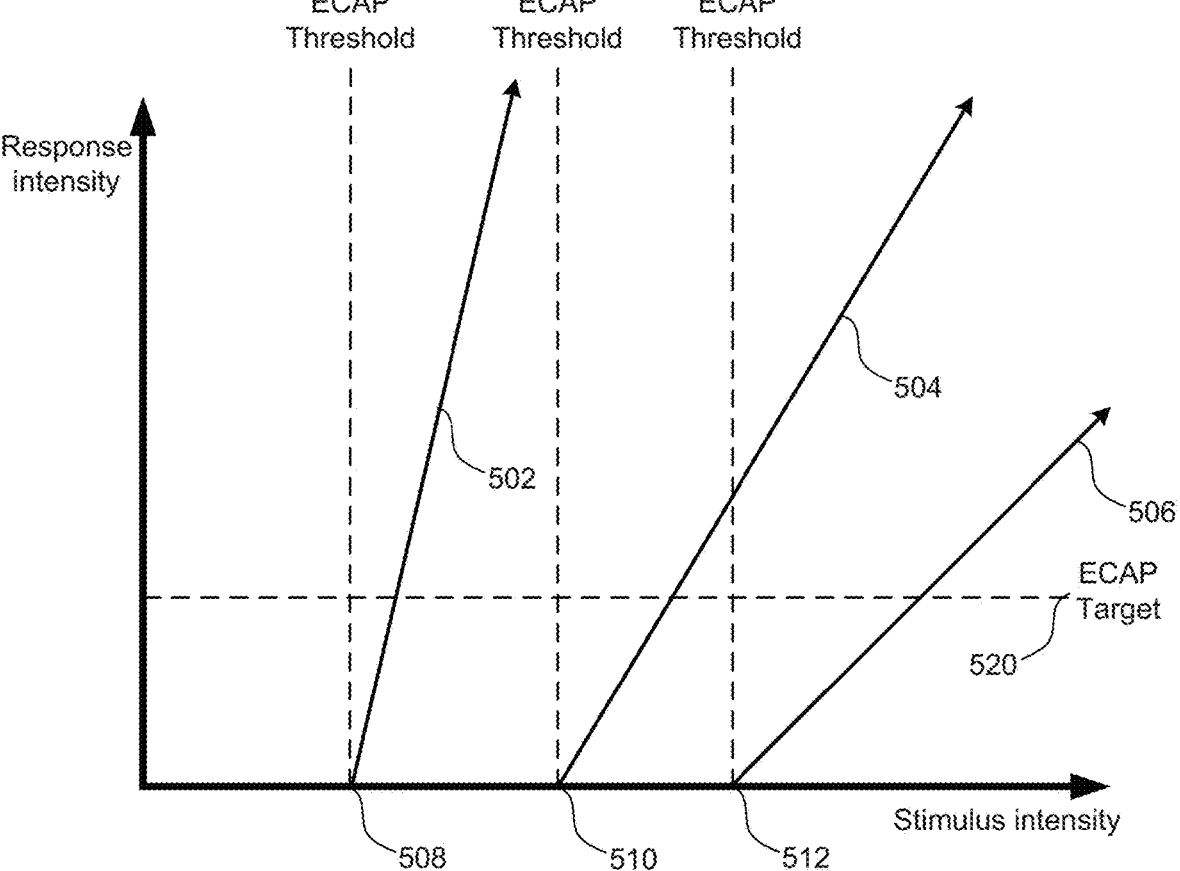
FIG. 4b illustrates the variation in the activation plots with changing posture of the patient.

FIG. 4b illustrates the variation in the activation plots with changing posture of the patient. A change in posture of the patient may cause a change in impedance of the electrode-tissue interface or a change in the distance between electrodes and the neurons. While the activation plots for only three postures, 502, 504 and 506, are shown in FIG. 4b, the activation plot for any given posture can lie between or outside the activation plots shown, on a continuously varying basis depending on posture. Consequently, as the patient's posture changes, the ECAP threshold changes, as indicated by the ECAP thresholds 508, 510, and 512 for the respective activation plots 502, 504, and 506. Additionally, as the patient's posture changes, the slope of the activation plot also changes, as indicated by the varying slopes of activation plots 502, 504, and 506. In general, as the distance between the stimulus electrodes and the spinal cord increases, the ECAP threshold increases and the slope of the activation plot decreases. The activation plots 502, 504, and 506 therefore correspond to increasing distance between stimulus electrodes and spinal cord, and decreasing patient sensitivity.

To keep the applied stimulus intensity within the therapeutic range as patient posture varies, in some implementations an implantable neuromodulation device such as the stimulator 100 may adjust the applied stimulus intensity based on a feedback variable that is determined from one or more measured ECAP characteristics. In one implementation, the device may adjust the stimulus intensity to maintain the measured ECAP amplitude at a target response intensity. For example, the device may calculate an error between a target ECAP amplitude and a measured ECAP amplitude, and adjust the applied stimulus intensity to reduce the error as much as possible, such as by adding the scaled error to the current stimulus intensity. A neuromodulation device that operates by adjusting the applied stimulus intensity based on a measured ECAP characteristic is said to be operating in closed-loop mode and will also be referred to as a closed-loop neural stimulation (CLNS) device. By adjusting the applied stimulus intensity to maintain the measured ECAP amplitude at an appropriate target response intensity, such as an ECAP target 520 illustrated in FIG. 4b, a CLNS device will generally keep the stimulus intensity within the therapeutic range as patient posture varies.

A CLNS device comprises a stimulator that takes a stimulus intensity value and converts it into a neural stimulus comprising a sequence of electrical pulses according to a predefined stimulation pattern. The stimulation pattern is parametrised by multiple stimulus parameters including stimulus amplitude, pulse width, number of phases, order of phases, number of stimulus electrode poles (two for bipolar, three for tripolar etc.), and stimulus rate or frequency. At least one of the stimulus parameters, for example the stimulus amplitude, is controlled by the feedback loop.

In an example CLNS system, a user (e.g. the patient or a clinician) sets a target response intensity, and the CLNS device performs proportional-integral-differential (PID) control. In some implementations, the differential contribution is disregarded and the CLNS device uses a first order integrating feedback loop. The stimulator produces stimulus in accordance with a stimulus intensity parameter, which evokes a neural response in the patient. The intensity of an evoked neural response (e.g. an ECAP) is detected, and its amplitude measured by the CLNS device and compared to the target response intensity.

The measured neural response intensity, and its deviation from the target response intensity, is used by the feedback loop to determine possible adjustments to the stimulus intensity parameter to maintain the neural response at the target intensity. If the target intensity is properly chosen, the patient receives consistently comfortable and therapeutic stimulation through posture changes and other perturbations to the stimulus/response behaviour.

Figure 5:
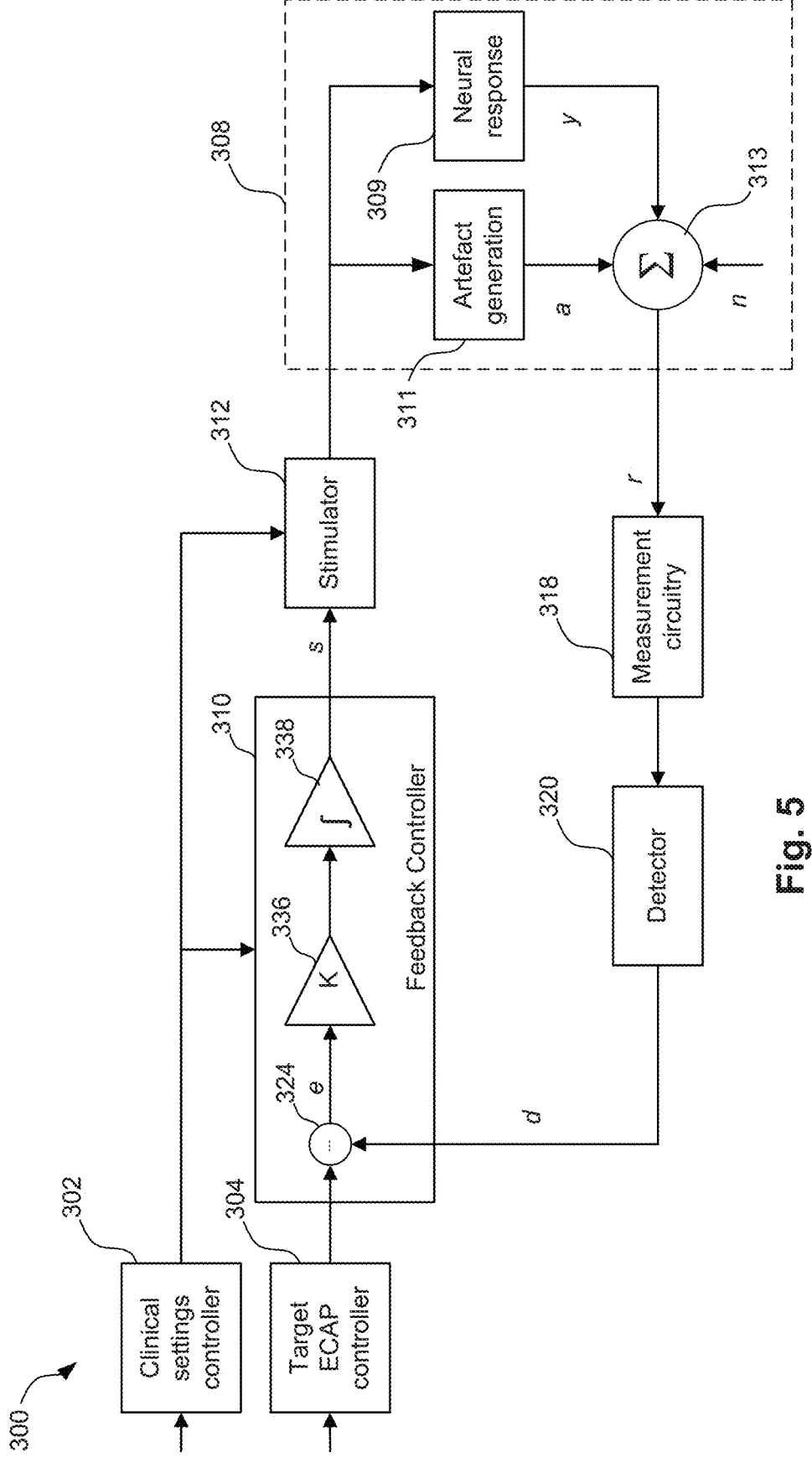
FIG. 5 is a schematic illustrating elements and inputs of a closed-loop neural stimulation system, according to one implementation of the present technology.

FIG. 5 is a schematic illustrating elements and inputs of a closed-loop neural stimulation (CLNS) system 300, according to one implementation of the present technology. The system 300 comprises a stimulator 312 which converts a stimulus intensity parameter (for example a stimulus current amplitude) s, in accordance with a set of predefined stimulus parameters, to a neural stimulus comprising a sequence of electrical pulses on the stimulus electrodes (not shown in FIG. 5). According to one implementation, the predefined stimulus parameters comprise the number and order of phases, the number of stimulus electrode poles, the pulse width, and the stimulus rate or frequency.

The generated stimulus crosses from the electrodes to the spinal cord, which is represented in FIG. 5 by the dashed box 308. The box 309 represents the evocation of a neural response y by the stimulus as described above. The box 311 represents the evocation of an artefact signal a, which is dependent on stimulus intensity and other stimulus parameters, as well as the electrical environment of the measurement electrodes. Various sources of measurement noise n, as well as the artefact a, may add to the evoked response intensity y at the summing element 313 to form the sensed signal r, including: electrical noise from external sources such as 50 Hz mains power; electrical disturbances produced by the body such as neural responses evoked not by the device but by other causes such as peripheral sensory input, EEG, EMG; and electrical noise from measurement circuitry 318.

The neural recruitment arising from the stimulus is affected by mechanical changes, including posture changes, walking, breathing, heartbeat and so on. Mechanical changes may cause impedance changes, or changes in the location and orientation of the nerve fibres relative to the electrode array(s). As described above, the intensity of the evoked response provides a measure of the recruitment of the fibres being stimulated. In general, the more intense the stimulus, the more recruitment and the more intense the evoked response. An evoked response typically has a maximum amplitude in the range of microvolts, whereas the voltage resulting from the stimulus applied to evoke the response is typically several volts.

Measurement circuitry 318, which may be identified with measurement circuitry 128, amplifies the sensed signal r (including evoked neural response, artefact, and measurement noise) and samples the amplified sensed signal r to capture a "signal window" comprising a predetermined number of samples of the amplified sensed signal r. The ECAP detector 320 processes the signal window and outputs a measured neural response intensity d. A typical number of samples in a captured signal window is 60. In one implementation, the neural response intensity comprises an ECAP amplitude. The measured response intensity d is input into the feedback controller 310. The feedback controller 310 comprises a comparator 324 that compares the measured response intensity d to a target ECAP amplitude as set by the target ECAP controller 304 and provides an indication of the difference between the measured response intensity d and the target ECAP amplitude. This difference is the error value, e.

The feedback controller 310 calculates an adjusted stimulus intensity parameter, s, with the aim of maintaining a measured response intensity d equal to the target ECAP amplitude. Accordingly, the feedback controller 310 adjusts the stimulus intensity parameter s to minimise the error value, e. In one implementation, the controller 310 utilises a first order integrating function, using a gain element 336 and an integrator 338, in order to provide suitable adjustment to the stimulus intensity parameters. According to such an implementation, the current stimulus intensity parameter s may be computed by the feedback controller 310 as $$s = \int Ke \, dt \qquad (2)$$

where K is the gain of the gain element 336 (the controller gain). This relation may also be represented as $$\delta s = Ke$$

where $\delta s$ is an adjustment to the current stimulus intensity parameter s.

A target ECAP amplitude is input to the comparator 324 via the target ECAP controller 304. In one embodiment, the target ECAP controller 304 provides an indication of a specific target ECAP amplitude. In another embodiment, the target ECAP controller 304 provides an indication to increase or to decrease the present target ECAP amplitude. The target ECAP controller 304 may comprise an input into the neuromodulation device, via which the patient or clinician can input a target ECAP amplitude, or indication thereof. The target ECAP controller 304 may comprise memory in which the target ECAP amplitude is stored, and from which the target ECAP amplitude is provided to the feedback controller 310.

A clinical settings controller 302 provides clinical settings to the system 300, including the gain K for the gain element 336 and the stimulus parameters for the stimulator 312. The clinical settings controller 302 may be configured to adjust the gain K of the gain element 336 to adapt the feedback loop to patient sensitivity. The clinical settings controller 302 may comprise an input into the neuromodulation device, via which the patient or clinician can adjust the clinical settings. The clinical settings controller 302 may comprise memory in which the clinical settings are stored, and are provided to components of the system 300.

In some implementations, two clocks (not shown) are used, being a stimulus clock operating at the stimulus frequency (e.g. 60 Hz) and a sample clock for sampling the sensed signal r (for example, operating at a sampling frequency of 10 kHz). As the ECAP detector 320 is linear, only the stimulus clock affects the dynamics of the CLNS system 300. On the next stimulus clock cycle, the stimulator 312 outputs a stimulus in accordance with the adjusted stimulus intensity s. Accordingly, there is a delay of one stimulus clock cycle before the stimulus intensity is updated in light of the error value e.

Figure 7:
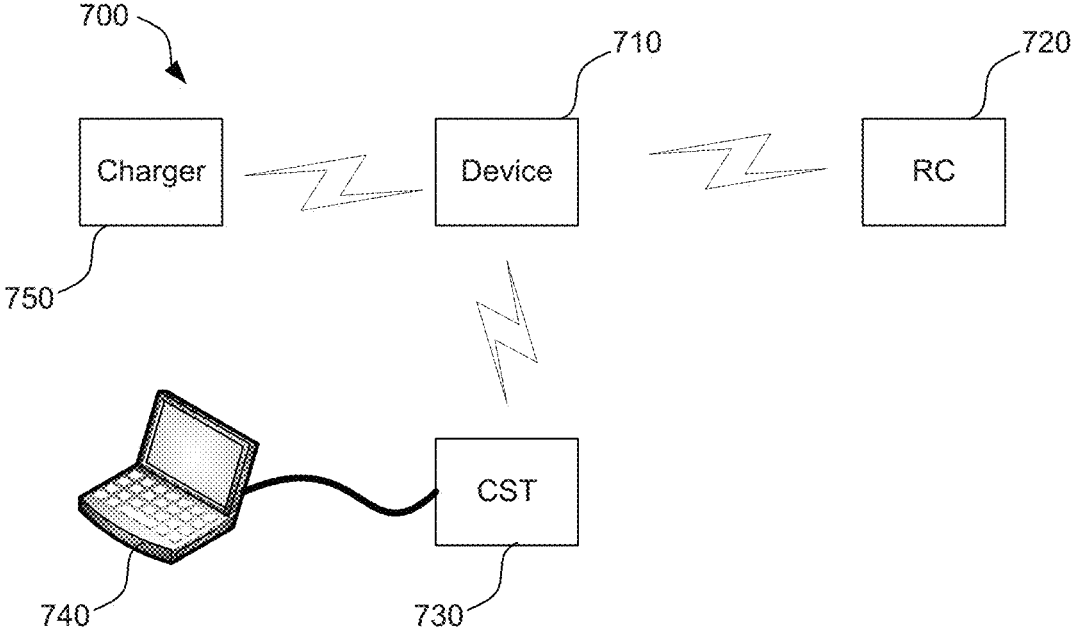
FIG. 7 is a block diagram of a neural stimulation therapy system including the implanted stimulator of FIG. 1 according to one implementation of the present technology.

FIG. 7 is a block diagram of a neural stimulation system 700. The neural stimulation system 700 is centred on a neuromodulation device 710. In one example, the neuromodulation device 710 may be implemented as the stimulator 100 of FIG. 1, implanted within a patient (not shown). The neuromodulation device 710 is connected wirelessly to a remote controller (RC) 720. The remote controller 720 is a portable computing device that provides the patient with control of their stimulation in the home environment by allowing control of the functionality of the neuromodulation device 710, including one or more of the following functions: enabling or disabling stimulation; adjustment of stimulus intensity or target neural response intensity; and selection of a stimulation control program from the control programs stored on the neuromodulation device 710.

The charger 750 is configured to recharge a rechargeable power source of the neuromodulation device 710. The recharging is illustrated as wireless in FIG. 7 but may be wired in alternative implementations.

The neuromodulation device 710 is wirelessly connected to a Clinical System Transceiver (CST) 730. The wireless connection may be implemented as the transcutaneous communications channel 190 of FIG. 1. The CST 730 acts as an intermediary between the neuromodulation device 710 and the Clinical Interface (CI) 740, to which the CST 730 is connected. A wired connection is shown in FIG. 7, but in other implementations, the connection between the CST 730 and the CI 740 is wireless.

The CI 740 may be implemented as the external computing device 192 of FIG. 1. The CI 740 is configured to program the neuromodulation device 710 and recover data stored on the neuromodulation device 710. This configuration is achieved by program instructions collectively referred to as the Clinical Programming Application (CPA) and stored in an instruction memory of the CI 740.

The Assisted Programming System

As mentioned above, obtaining patient feedback about their sensations is important during programming of closed-loop neural stimulation therapy, but mediation by trained clinical engineers is expensive and time-consuming. It would therefore be advantageous if patients could program their own implantable device themselves, or with some assistance from a clinician. However, interfaces for current programming systems are non-intuitive and generally unsuitable for direct use by patients because of their technical nature. There is therefore a need for a CPA to be as intuitive for non-technical users as possible while avoiding discomfort to the patient.

Implementations of an Assisted Programming System (APS) according to the present technology are generally configured to meet this need. In some implementations, the APS comprises two elements: the Assisted Programming Module (APM), which forms part of the CPA, and the Assisted Programming Firmware (APF), which forms part of the control programs 122 executed by the controller 116 of the electronics module 110. The data obtained from the patient is analysed by the APM to determine the parameters and settings for the neural stimulation therapy to be delivered by the stimulator 100. The APF is configured to complement the operation of the APM by responding to commands issued by the APM via the CST 730 to the stimulator 100 to deliver specified stimuli to the patient, and by returning, via the CST 730, measurements of neural responses to the delivered stimuli.

In other implementations, all the processing of the APS according to the present technology is done by the APF. In other words, the data obtained from the patient is not passed to the APM, but is analysed by the APF to determine the parameters and settings for the closed-loop neural stimulation therapy to be delivered by the stimulator 100.

In implementations of the APS in which the APM analyses the data from the patient, the APS instructs the device 710 to capture and return signal windows to the CI 740 via the CST 730. In such implementations, the device 710 captures the signal windows using the measurement circuit 128 and bypasses the ECAP detector 320, storing the data representing the raw signal windows temporarily in memory 118 before transmitting the data representing the captured signal windows to the APS for analysis.

Following the processing, the APS may load the determined program onto the device 710 to govern subsequent neural stimulation therapy. In one implementation, the program comprises clinical settings 121, also referred to as therapy parameters, that are input to the neuromodulation device by, or stored in, the clinical settings controller 302. The patient may subsequently control the device 710 to deliver the therapy according to the determined program using the remote controller 720 as described above. In one implementation, the remote controller 720 may control the target ECAP amplitude for the CLNS system 300 via the input to the target ECAP controller 304. The determined program may also, or alternatively, be loaded into the CPA for validation and modification.

Setting Controller Gain

Figure 8:
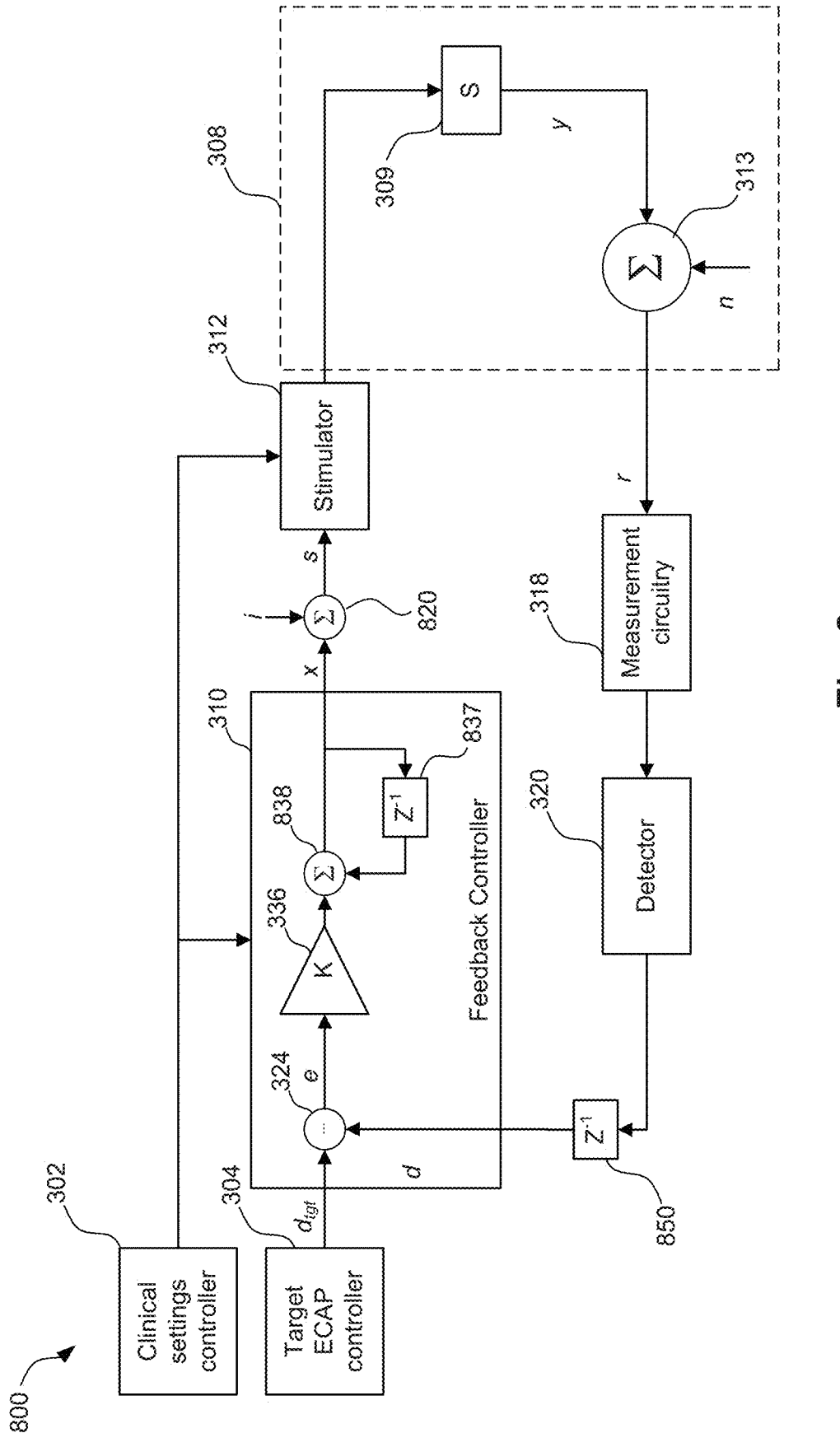
FIG. 8 is a schematic illustrating an explicitly discrete implementation of the CLNS system of FIG. 5.

FIG. 8 is a schematic illustrating an explicitly discrete-time implementation 800 of the CLNS system 300 of FIG. 5. The artefact-evoking element 311 has been removed for simplicity. The integrator 338 in the feedback controller 310 of the CLNS system 300 has been replaced by a summing element 838 that adds the gain-multiplied error term Ke from the gain controller 336 to the previous value (obtained from a delay element 837 applied to the current value) of the stimulus intensity parameter, now labelled as x, to obtain the current value of the stimulus intensity parameter x. The patient box 309 is modelled by a linear scalar S representing the baseline patient sensitivity in a certain-posture, i.e. the rate of change of evoked neural response intensity y with respect to stimulus intensity s. The system 800 also includes a stimulus intensity perturbation i that is added to the stimulus intensity parameter x determined by the feedback controller 310 by the summing element 820 to obtain the applied stimulus intensity parameters. The neural response intensity from the detector 320 is delayed by one sample by a delay element 850 before becoming the measured neural response intensity d (also referred to as the feedback variable) that is compared with the target neural response intensity $d_{tgt}$ by the comparator 324. The sampling frequency $f_s$ of the discrete-time CLNS system 800 is the stimulus frequency.

As illustrated in FIG. 4b, the activation plot varies significantly with posture. For certain patients, the activation plot even varies significantly within a single posture as a result of cyclical anatomic events such as heartbeat and breathing, which perturb the distance between the electrode array and the spinal cord. Such cyclical anatomic perturbations may be referred to as "posture waves" as they mimic the effects of a periodic variation of posture. A posture wave may be modelled as a periodic perturbation i of stimulus intensity with amplitude $\Delta i$ at a posture wave frequency $f_p$. The periodic perturbation i of stimulus intensity is added to the stimulus intensity parameter x by the summing element 820, as illustrated in FIG. 8.

Assuming the detector 320 and measurement circuitry 318 between them have unity gain, the transfer function from the target neural response intensity $d_{tgt}$ to the measured neural response intensity d is given in the Z-transform domain by $$\frac{d}{d_{tgt}} = \frac{Gz^{-1}}{1 - (1 - G)z^{-1}} \tag{3}$$

where G is the loop gain, defined as the product KS of the controller gain K and the patient sensitivity S.

The transfer function from the stimulus intensity perturbation i to the measured neural response intensity d is given in the Z-transform domain by $$\frac{d}{i} = Sz^{-1} \frac{1 - z^{-1}}{1 - (1 - G)z^{-1}} \tag{4}$$

The transfer function from the measurement noise n to the measured neural response intensity d is given in the Z-transform domain by $$\frac{d}{n} = \frac{z^{-1}(1 - z^{-1})}{1 - (1 - G)z^{-1}} \tag{5}$$

The transfer function from the measurement noise n to the evoked neural response intensity y is given in the Z-transform domain by $$\frac{y}{n} = \frac{-Gz^{-1}}{1 - (1 - G)z^{-1}} \tag{6}$$

It may be seen that Equation (3) and (6) represent low-pass filters, with a cutoff frequency $f_c$ that varies with loop gain G according to the following relation:

$$\cos\omega = \frac{(G + 1)^2 - 3}{2(G - 1)} \tag{7}$$

where $\omega = 2\pi f_c/f_s$.

It may be shown using Equation (3) that the response $d_u[n]$ of the neural response intensity d to a unit step u[n] in the target intensity $d_{tgt}$ is given by:

$$d_u[n] = u[n-1](1 - (1 - G)^n) \tag{8}$$

which is an exponential rise to unity with time constant t given by:

$$\tau = -\frac{1}{f_s \log(1 - G)} \tag{9}$$

Equation (9) shows that the step response rises faster (shorter time constant r) as the loop gain G increases. For this reason, loop gain G is sometimes referred to as the loop speed. The loop gain G may be measured from the first few samples of the step response $d_u[n]$ using the following relation derived from Equation (8):

$$G = \frac{d_u[n + 3] - 2d_u[n + 2] + d_u[n + 1]}{d_u[n + 1] - d_u[n + 2]} \tag{10}$$

It may further be shown using Equation (5) that, on the assumption that the measurement noise n is white, i.e. uniformly distributed in the frequency domain, a response noise amplification ratio $R_n$, defined as the ratio of the closed-loop RMS noise (standard deviation) in the measured neural response intensity d to the open-loop RMS noise in d, may be computed as:

$$R_n = \sqrt{\frac{2}{2 - G}} \tag{11}$$

which increases from unity at G=0 (open-loop) to infinity as loop gain G approaches 2. Therefore as loop gain G increases, measurement noise n is increasingly amplified.

It may also be shown using Equation (6) that, on the assumption that the measurement noise n is white, the amount of noise in the stimulus intensity x, which may be perceived by the patient, is a function of the measurement signal to noise ratio, i.e. the measured neural response intensity d divided by the variance of the measurement noise n, as well as the loop gain G. In an alternative formulation of the noise amplification ratio, a quantity $R_x$, referred to as the stimulus noise amplification ratio, and defined as the standard deviation $\sigma_x$ of the noise in the stimulus intensity x as a proportion of the therapeutic range $\Delta s$, may be computed as:

$$R_x = \frac{\sigma_x}{\Delta s} = \frac{1}{2 \cdot SNR}\sqrt{\frac{G}{2 - G}} \tag{12}$$

where SNR is the measurement signal to noise ratio. The stimulus noise amplification ratio $R_x$ increases from zero at G=0 (open-loop) to infinity as loop gain G approaches 2.

By contrast, Equation (4) represents a high-pass filter with a cutoff frequency that also varies with loop gain G. It may be shown using Equation (4) that, assuming the posture wave may be modelled as a periodic stimulus intensity perturbation i with amplitude $\Delta i$ and frequency $f_p$, the amplitude $\Delta d$ of variation of the resulting neural response intensity d may be computed as:

$$\Delta d = S\Delta i \sqrt{\frac{2 - 2\cos(r)}{1 + (G - 1)^2 + 2(G - 1)\cos(r)}} \tag{13}$$

where $r = \frac{2\pi f_p}{f_s}$.

Using equation (13), it may be shown that the posture wave amplification ratio $R_p$, defined as the ratio of posture wave variation in neural response intensity d from closed-loop to open-loop (G=0), is given by:

$$R_p = \frac{r}{\sqrt{r^2 + G^2}} \tag{14}$$

which decreases from unity at open loop (G=0) toward zero as loop gain G increases.

Viewing Equations (11) and (14) together, it may be seen that increasing loop gain G towards the stability limit of 2 increases noise amplification (thereby increasing noise in the neural response intensity) while decreasing posture wave amplification (thereby decreasing posture-wave-induced variation in the neural response intensity). The choice of controller gain K is therefore a trade-off between the amount of noise in the patient's neural response intensity and the amount of variation in the neural response intensity induced by the posture wave. A figure-of-merit for a CLNS may be defined as the total amplification $R_t$, where $R_t$ is the Euclidean length of a vector $[R_p, \sqrt{\lambda}R_n]$:

$$R_t^2 = R_p^2 + \lambda R_n^2 \tag{15}$$

The parameter $\lambda$ balances the relative importance of noise and posture wave amplification in the total amplification $R_t$. The minimising loop gain $G_{opt}$ is the value of G at which the total amplification $R_t$, or more conveniently the square $R_t^2$ of the total amplification, is minimised. It may be shown by substitution of Equations (11) and (14) into Equation (15) and differentiation with respect to G that the minimising loop gain $G_{opt}$ is a solution to a quartic equation in G whose coefficients involve r and the balancing parameter λ:

$$a(r,\lambda)G^4 - b(r,\lambda)G^3 + c(r,\lambda)G^2 - d(r,\lambda)G + d(r,\lambda) = 0 \qquad (16)$$

This quartic equation may be solved analytically or numerically for the minimising loop gain $G_{opt}$ if r and λ are known. Given that the minimising loop gain $G_{opt}$ must lie in the range [1, 2], a root-finding algorithm such as Newton-Raphson may be used to find a numerical solution for $G_{opt}$. However, the preferred balancing parameter λ for a particular patient is not known.

In some implementations of programming a CLNS system 300, the balancing parameter λ may be chosen as a function of the target response intensity $d_{tgt}$. Targets that are closer to the noise level of the measurement circuitry 318 will be suitable for a stronger weighting towards decreased noise amplification (a higher value of λ) since the patient will receive higher stimulus intensity noise relative to the achieved recruitment level. Conversely, the noise amplification becomes less important for high targets and the patient may benefit from the decreased posture wave amplification achieved by a lower value of λ.

Reordering the terms in the quartic Equation (16) for the minimising loop gain $G_{opt}$ gives an expression for the balancing parameter λ in terms of r and the minimising loop gain $G_{opt}$.

The response noise amplification ratio $R_n$, the stimulus noise amplification ratio $R_x$, the posture wave amplification ratio $R_p$, and the total amplification $R_t$, are all examples of a general loop characteristic referred to herein as the amplification parameter.

Methods and systems of programming a neuromodulation device according to some aspects of the present technology select an "optimal" controller gain $K_{opt}$ as the value of controller gain K that yields a loop characteristic that is equal, or substantially equal, to a predetermined trade-off value of the loop characteristic. The loop characteristic may be the loop gain G, the cutoff frequency $f_c$, the time constant t, the response noise amplification ratio $R_n$, the stimulus noise amplification ratio $R_x$, the posture wave amplification ratio $R_p$, the total amplification Ri, the balancing parameter λ, or another variable that characterises closed loop performance and is therefore related to the controller gain K. The optimal controller gain $K_{opt}$ may be either computed from the predetermined trade-off value using the equations (7) to (16) above, or obtained empirically using measurements of the loop characteristic at different values of controller gain K.

In some implementations, the predetermined trade-off value of the loop characteristic has been previously derived from data of successfully programmed patients. The data may comprise a set of N vectors $\{V_i, i=1, \ldots, N\}$ with each vector $V_i$ corresponding to a set of patient parameters for the patient indexed i. The components of the vector $V_i$ are the controller gain $K_i$ with which the patient has been programmed, and measurements from the patient, including one or more of the sensitivity $S_i$, the stimulus frequency $f_{si}$, the measurement signal to noise ratio $SNR_i$, and the posture wave frequency $f_{pi}$. The posture wave frequency $f_{pi}$ may be obtained during programming using an external sensor such as a heart rate monitor (for heart rate), spirometer (for breathing rate), or activity monitor (for gait frequency). Alternatively, the posture wave frequency may be obtained by spectral analysis of the feedback variable d.

It may be presumed that the data set of vectors $\{V_i\}$ represent acceptable trade-offs that have been arrived at by manual adjustment based on patient feedback about their sensations of noise, posture wave, loop speed, etc. The data set of vectors $\{V_i\}$ may be used to derive a set of corresponding values of the loop characteristic using the equations (7) to (16) above. The predetermined trade-off value may then be derived as a representative value of the set of values of the loop characteristic, for example a mean, median, or mode of the distribution of values of the loop characteristic.

In one implementation of deriving the predetermined trade-off value, the loop gain $K_i$ and the sensitivity $S_i$ from each vector $V_i$ are multiplied together to obtain a set of values of loop gain $\{G_i\}$. A representative loop gain $\overline{G}$ is derived from the set of values of loop gain $\{G_i\}$, for example by averaging the set of values of loop gain $\{G_i\}$. The representative loop gain $\overline{G}$ may be later used as the predetermined trade-off value to obtain the optimal controller gain $K_{opt}$ as described below.

In one implementation of deriving the predetermined trade-off value, the loop gain $K_i$ and the sensitivity $S_i$ from each vector $V_i$ are multiplied together to obtain a set of values of loop gain $\{G_i\}$. The set of values of loop gain $\{G_i\}$ and the stimulus frequencies $f_{si}$ from each vector Vt are fed into Equation (7) to obtain a set of values of loop cutoff frequency $\{f_{ci}\}$. A representative cutoff frequency $\overline{f_c}$ is derived from the set of values of cutoff frequency $\{f_{ci}\}$, for example by averaging the set of values of cutoff frequency $\{f_{ci}\}$. The representative cutoff frequency $\overline{f_c}$ may be later used as the predetermined trade-off value to obtain the optimal controller gain Kop, as described below.

In one implementation of deriving the predetermined trade-off value, the loop gain Kt and the sensitivity $S_i$ from each vector Vt are multiplied together to obtain a set of values of loop gain $\{G_i\}$. The set of values of loop gain $\{G_i\}$ and the stimulus frequencies $f_{si}$ from each vector Vt are fed into Equation (9) to obtain a set of values of time constant $\{t_i\}$. A representative time constant f is derived from the set of values of time constant $\{\tau_i\}$, for example by averaging the set of values of time constant $\{\tau_i\}$. The representative time constant f may be later used as the predetermined trade-off value to obtain the optimal controller gain $K_{opt}$ as described below.

In one implementation of deriving the predetermined trade-off value, the loop gain $K_i$ and the sensitivity $S_i$ from each vector Vt are multiplied together to obtain a set of values of loop gain $\{G_i\}$. The set of values of loop gain $\{G_i\}$, and optionally the measurement SNRs $\{SNR_i\}$ from each vector $V_i$, are fed into Equation (11) or Equation (12) to obtain a set of values of response or stimulus noise amplification ratio $\{R_{ni}\}$ or $\{R_{xi}\}$. A representative noise amplification ratio $\overline{R_n}$ or $\overline{R_x}$ is derived from the set of values of noise amplification ratio $\{R_{ni}\}$ or $\{R_{xi}\}$, for example by averaging the set of values of noise amplification ratio $\{R_{ni}\}$ or $\{R_{xi}\}$. The representative noise amplification ratio $\overline{R_n}$ or $\overline{R_x}$ may be later used as the predetermined trade-off value to obtain the optimal controller gain $K_{opt}$ as described below.

In one implementation of deriving the predetermined trade-off value, the loop gain $K_i$ and the sensitivity $S_i$ from each vector $V_i$ are multiplied together to obtain a set of values of loop gain $\{G_i\}$. The set of values of loop gain $\{G_i\}$ and the posture wave and stimulus frequencies $f_{pi}$ and $f_{si}$ from each vector $V_i$ are fed into Equation (14) to obtain a set of values of posture wave amplification ratio $\{R_{pi}\}$. A representative posture wave amplification ratio R, is derived from the set of values of posture wave amplification ratio $\{R_{pi}\}$, for example by averaging the set of values of posture wave amplification ratio $\{R_{pi}\}$. The representative posture wave amplification ratio R, may be later used as the predetermined trade-off value to obtain the optimal controller gain $K_{opt}$ as described below.

In one implementation of deriving the predetermined trade-off value, the loop gain $K_i$ and the sensitivity $S_i$ from each vector $V_i$ are multiplied together to obtain a set of values of loop gain $\{G_i\}$. The set of values of loop gain $\{G_i\}$, and optionally the measurement SNRs $\{SNR_i\}$ from each vector $V_i$, are fed into Equation (11) or Equation (12) to obtain a set of values of noise amplification ratio $\{R_{ni}\}$. The set of values of loop gain $\{G_i\}$ and the posture wave and stimulus frequencies $f_{pi}$ and $f_{si}$ from each vector $V_i$ are fed into Equation (14) to obtain a set of values of posture wave amplification ratio $\{R_{pi}\}$. The sets of values of noise amplification ratio $\{R_{ni}\}$ and posture wave amplification ratio $\{R_{ti}\}$ are fed into Equation (15) along with a predetermined value of the balancing parameter $\lambda$ (e.g. one obtained from the target neural response intensity as described above) to obtain a set of values of total amplification $\{R_{ti}\}$. A representative total amplification $\overline{R}_t$ is derived from the set of values of total amplification $\{R_{ti}\}$, for example by averaging the set of values of total amplification $\{R_{ti}\}$. The representative total amplification $\overline{R}_t$ may be later used as the predetermined trade-off value to obtain the optimal controller gain $K_{opt}$ as described below.

In one implementation of deriving the predetermined trade-off value, the loop gain $K_i$ and the sensitivity $S_i$ from each vector $V_i$ are multiplied together to obtain a set of values of loop gain $\{G_i\}$. The set of values of loop gain $\{G_i\}$ and the posture wave and stimulus frequencies $f_{pi}$ and $f_{si}$ from each vector $V_i$ are fed into Equation (16) to obtain a set of values of the balancing parameter $\lambda$. A representative balancing parameter $\overline{\lambda}$ is derived from the set of values of balancing parameter $\{\lambda_i\}$, for example by averaging the set of values of balancing parameter $\{\lambda_i\}$. The representative balancing parameter $\overline{\lambda}$ may be later used as the predetermined trade-off value to obtain the optimal controller gain $K_{opt}$ as described below.

Figure 9:
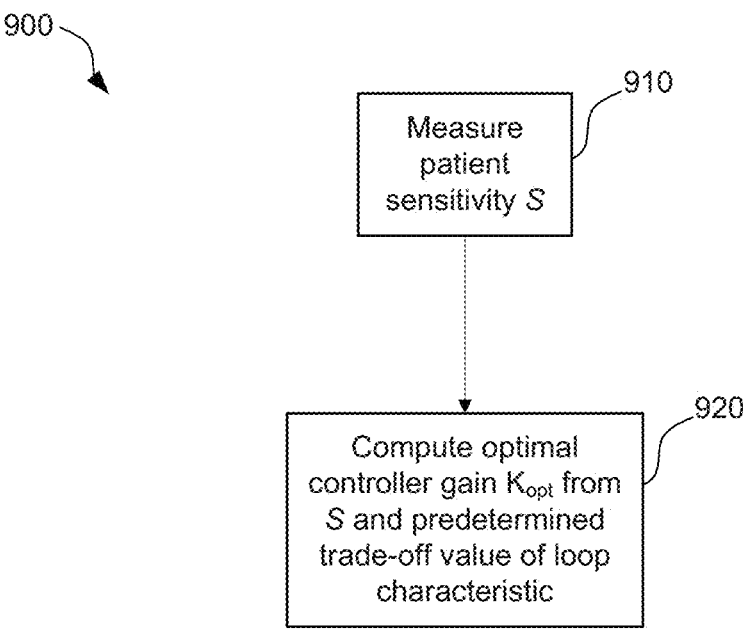
FIG. 9 is a flow chart illustrating a calculational method of selecting an optimal controller gain according to one aspect of the present technology.

FIG. 9 is a flow chart illustrating a calculational method 900 of selecting an optimal controller gain $K_{opt}$ according to one aspect of the present technology. The method 900 may be carried out by the APS as part of the assisted programming of a patient.

The method 900 starts at step 910, which measures the patient sensitivity S. As mentioned above, the patient sensitivity is the slope of the activation plot. In one implementation, step 910 makes multiple measurements of neural response intensity y at different values of stimulus intensity s, and fits a piecewise linear model to the pairs $\{(s_i, y_i)\}$ of neural response intensity measurements $y_i$ and corresponding stimulus intensity values $s_i$ such as described above in relation to Equation (1). Other methods of estimating the patient sensitivity S are disclosed, for example, in International Patent Application no. PCT/AU2022/051556, the contents of which are herein incorporated by reference.

Step 920 then computes the optimal controller gain $K_{opt}$ from the measured patient sensitivity S and the predetermined trade-off value of the loop characteristic.

One implementation of step 920, in which the predetermined trade-off value is a representative value $\overline{G}$ of loop gain, computes the optimal controller gain $K_{opt}$ by dividing the representative loop gain value $\overline{G}$ by the measured patient sensitivity S.

One implementation of step 920, in which the predetermined trade-off value is a representative value $\overline{f}_c$ of loop cutoff frequency, computes the optimal controller gain Kop, by inverting Equation (7) to compute an optimal loop gain $G_{opt}$ from the representative value $\overline{f}_c$ of loop cutoff frequency and the stimulus frequency $f_s$. Step 920 then computes the optimal controller gain $K_{opt}$ by dividing the optimal loop gain $G_{opt}$ by the measured patient sensitivity S.

One implementation of step 920, in which the predetermined trade-off value is a representative value f of loop time constant, computes the optimal controller gain Kop, by inverting Equation (9) to compute an optimal loop gain $G_{opt}$ from the representative value f of loop time constant and the stimulus frequency $f_s$. Step 920 then computes the optimal controller gain $K_{opt}$ by dividing the optimal loop gain $G_{opt}$ by the measured patient sensitivity S.

One implementation of step 920, in which the predetermined trade-off value is a representative value $R_n$ of noise amplification ratio, computes the optimal controller gain $K_{opt}$ by inverting Equation (11) or Equation (12) to compute an optimal loop gain $G_{opt}$ from the representative value $R_n$ of noise amplification ratio and (when using Equation (12)) the measurement signal to noise ratio SNR. (In the latter implementation, step 910 may also measure the measurement signal to noise ratio SNR.) Step 920 then computes the optimal controller gain $K_{opt}$ by dividing the optimal loop gain $G_{opt}$ by the measured patient sensitivity S.

One implementation of step 920, in which the predetermined trade-off value is a representative value R, of posture wave amplification ratio, computes the optimal controller gain $K_{opt}$ by inverting Equation (14) to compute an optimal loop gain $G_{opt}$ from the representative value R, of posture wave amplification ratio, the stimulus frequency $f_s$, and the posture wave frequency $f_p$. Step 920 then computes the optimal controller gain $K_{opt}$ by dividing the optimal loop gain $G_{opt}$ by the measured patient sensitivity S. In such an implementation, step 910 may also measure the posture wave frequency $f_p$. Step 910 may measure the posture wave frequency $f_p$ using an external sensor such as a heart rate monitor (for heart rate), spirometer (for breathing rate), activity monitor (for gait frequency). Alternatively, step 910 may measure the posture wave frequency by spectral analysis of the feedback variable d. Alternatively, step 910 may use a default value for the posture wave frequency $f_p$ such as 1.2 Hz for the heart rate.

In one implementation of step 920, the predetermined trade-off value is a representative value $R_t$ of the total amplification $R_t$. In such an implementation, step 920 computes an optimal loop gain $G_{opt}$ by inverting Equation (15) to compute an optimal loop gain $G_{opt}$ from the representative value $\overline{R}_t$ of total amplification, the stimulus frequency $f_s$, the posture wave frequency $f_p$, and the predetermined value of the balancing parameter $\lambda$, used to compute the representative value $\overline{R}_t$ of total amplification. Note that inverting Equation (15) involves solving a cubic equation in G, which may be done either analytically or numerically, e.g. using a Newton-Raphson algorithm. Step 920 then computes the optimal controller gain $K_{opt}$ by dividing the optimal loop gain $G_{opt}$ by the measured patient sensitivity S. In such an implementation, step 910 may also measure the posture wave frequency $f_p$ as described above.

In one implementation of step 920, the predetermined trade-off value is a representative value $\overline{\lambda}$ of the balancing parameter for calculating the total amplification $R_t$. In such an implementation, step 920 computes an optimal loop gain $G_{opt}$ from the representative value $\overline{\lambda}$ of the balancing parameter, the stimulus frequency $f_s$, and the posture wave frequency $f_p$ by solving the quartic Equation (16) for G, either analytically or numerically, e.g. using a Newton-Raphson algorithm. Step 920 then computes the optimal controller gain $K_{opt}$ by dividing the optimal loop gain $G_{opt}$ by the measured patient sensitivity S. In such an implementation, step 910 may also measure the posture wave frequency $f_p$ as described above.

Figure 10:
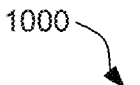
FIG. 10 is a flow chart illustrating an empirical method of selecting an optimal controller gain $K_{opt}$ according to a further aspect of the present technology.
Figure 10:
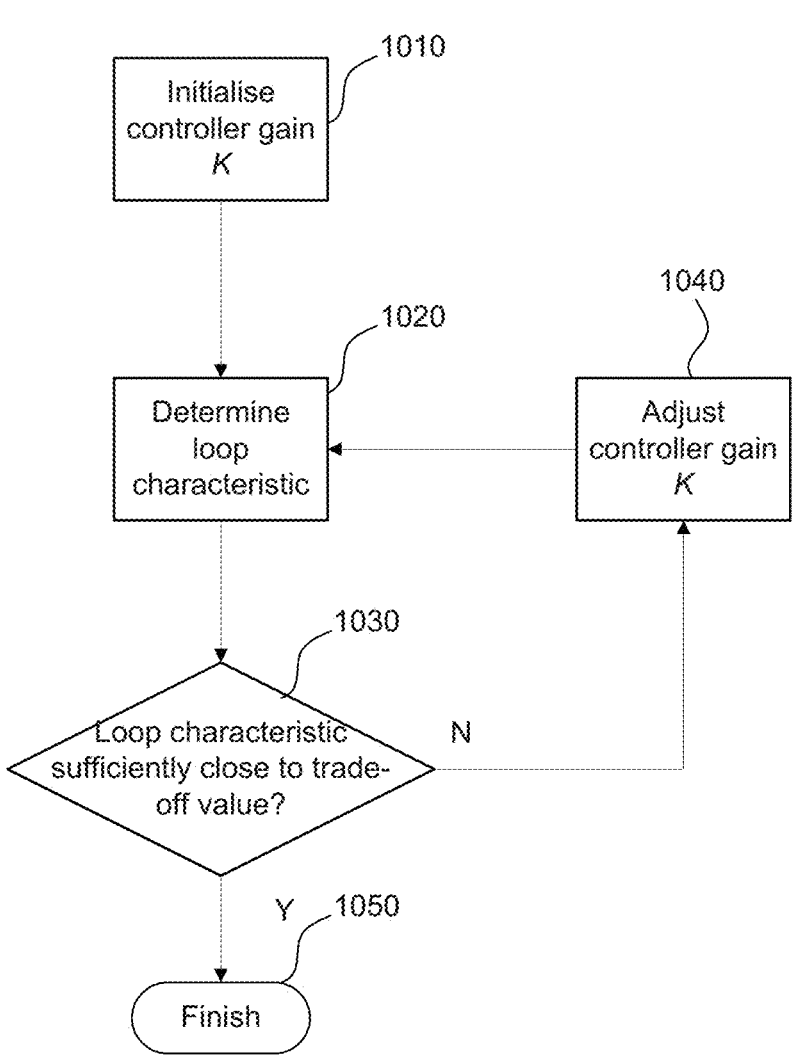

FIG. 10 is a flow chart illustrating an empirical method 1000 of selecting an optimal controller gain $K_{opt}$ according to a further aspect of the present technology. The method 1000 may be carried out by the APS as part of the assisted programming of a patient. The method 1000 does not require the initial measurement of patient sensitivity S. Instead, the method 1000 repeatedly measures a value of loop characteristic for different values of controller gain K, stopping when the measured value of the loop characteristic is within a predetermined distance from the predetermined trade-off value of the loop characteristic.

The method 1000 starts at step 1010, which initialises the controller gain K to an initial value, for example 1. Step 1020 then determines the loop characteristic.

In one implementation of step 1020 in which the loop characteristic is the loop gain, Equation (10) is applied to estimate the loop gain G from the response $d_u[n]$ to a step in the target intensity.

In another implementation of step 1020 in which the loop characteristic is the loop time constant t, Equation (10) is applied to estimate the loop gain G from the response $d_u[n]$ to a step in the target intensity. Equation (9) is then applied to compute the time constant $\tau_i$ from the estimated loop gain G and the stimulus frequency $f_s$. Alternatively, step 1020 may measure the time constant $\tau$ directly from the step response $d_u[n]$.

In another implementation of step 1020 in which the loop characteristic is the loop cutoff frequency $f_c$, Equation (10) is applied to estimate the loop gain G from the response $d_u[n]$ to a step in the target intensity. Equation (7) is then applied to estimate the cutoff frequency $f_c$ from the estimated loop gain G and the stimulus frequency $f_s$.

In another implementation of step 1020 in which the loop characteristic is a noise amplification ratio $R_n$ or $R_x$, Equation (10) is applied to estimate the loop gain G from the response $d_u[n]$ to a step in the target-intensity. Equation (11) or Equation (12) is then applied to estimate the noise amplification ratio $R_n$ or $R_x$ from the estimated loop gain G, and optionally and the measurement SNR. Alternatively, step 1020 may measure the response noise amplification ratio $R_n$ directly by measuring the ratio of the RMS noise in the measured neural response intensity d to the open-loop RMS noise in d. Alternatively, step 1020 may measure the stimulus noise amplification ratio $R_x$ directly by measuring the ratio of the standard deviation $\sigma_x$ of the noise in the stimulus intensity x, to the therapeutic range $\Delta s$. Alternatively, a closed-loop-to-open-loop ratio of noise statistics other than the RMS value may be measured and used as a proxy for the noise amplification ratio $R_n$ or $R_x$.

In another implementation of step 1020 in which the loop characteristic is the posture wave amplification ratio $R_p$, Equation (10) is applied to estimate the loop gain G from the response $d_u[n]$ to a step in the target intensity. Equation (14) is then applied to estimate the posture wave amplification ratio $R_p$ from the estimated loop gain G, the stimulus frequency $f_s$, and the posture wave frequency $f_p$. In such an implementation, step 1020 may also measure the posture wave frequency $f_p$ as described above. Alternatively, step 1020 may use a default value for the posture wave frequency $f_p$ such as 1.2 Hz for the heart rate. Alternatively, step 1020 may measure the posture wave amplification ratio $R_p$ directly by measuring the ratio of the amplitude of variation at the posture wave frequency $f_p$ in the measured neural response intensity d to the open-loop amplitude of variation in d.

In another implementation of step 1020 in which the loop characteristic is the total amplification $R_t$, Equation (10) is applied to estimate the loop gain G from the response $d_u[n]$ to a step in the target intensity. Equation (11) or Equation (12) is then applied to estimate the noise amplification ratio $R_n$ or $R_x$ from the estimated loop gain G. Alternatively, step 1020 may measure the response noise amplification ratio $R_n$ directly by measuring the ratio of the RMS noise in the measured neural response intensity d to the open-loop RMS noise in d. Alternatively, step 1020 may measure the stimulus noise amplification ratio $R_x$ directly by measuring the ratio of the standard deviation ax of the noise in the stimulus intensity x, to the therapeutic range $\Delta s$. Equation (14) is then applied to estimate the posture wave amplification ratio $R_p$ from the estimated loop gain G, the stimulus frequency $f_s$, and the posture wave frequency $f_p$. In such an implementation, step 1020 may also measure the posture wave frequency $f_p$ as described above. Alternatively, step 1020 may use a default value for the posture wave frequency $f_p$ such as 1.2 Hz for the heart rate. Alternatively, step 1020 may measure the posture wave amplification ratio $R_p$ directly by measuring the ratio of the amplitude of variation at the posture wave frequency $f_p$ in the measured neural response intensity d to the open-loop amplitude of variation in d. Step 1020 then applies Equation (15) and the predetermined value of the balancing parameter $\lambda$ used to compute the representative value $\overline{R}_t$ of total amplification to compute the total amplification $R_t$.

Step 1030 then checks whether the measured value of the loop characteristic is within a predetermined distance from the predetermined trade-off value of the loop characteristic. If so ("Y"), the method 1000 ends at step 1050 with the current value of the controller gain K being taken as the optimal value $K_{opt}$ of the controller gain. If not ("N"), step 1040 adjusts the controller gain K so as to bring the measured value of the loop characteristic closer to the predetermined trade-off value. The method 1000 then returns to step 1020.

Another implementation of an empirical method that is specific to the case where the loop characteristic is the total amplification $R_t$ is similar to the method 1000. However, step 1030, instead of checking whether the total amplification $R_t$ is within a predetermined distance from a predetermined trade-off value, checks whether the measured value of the total amplification R, has reached a local minimum. If not ("N"), step 1040 then adjusts the controller gain K so as to bring the measured value of the total amplification R, closer to a local minimum using one of a variety of objective function minimisation strategies such as the gradient algorithm.

In other implementations of these aspects of the present technology, the feedback controller 310 may have multiple parameters to be set rather than a single parameter (gain K) as described above. One such implementation uses a proportional-integral-differential (P-I-D) controller, which has three parameters (the scalars on the error, its integral, and its derivative). In such implementations, the optimal controller parameters may be set so as to bring a measured or computed value of a loop characteristic close to a predetermined representative value of the loop characteristic in similar fashion to the above description of setting a single controller parameter (the controller gain). Alternatively, representative values of multiple loop characteristics may be jointly achieved by appropriate optimisation of the vector of controller parameters. For an arbitrary system transfer function, the posture wave amplification ratio $R_p$ and noise amplification ratio $R_n$ or $R_x$ could be derived as a function of the controller parameters. A multidimensional derivative with respect to all of the controller parameters of the total amplification $R_t$ could then be derived, and used to find the controller parameter vector that minimizes the total amplification $R_t$ with respect to all of the controller parameters jointly.

In methods and systems according to a further aspect of the present technology, the optimal controller gain may be set based on qualitative patient feedback about their sensations while the controller gain is being adjusted. In one such implementation, the APS may render a user interface on the CI 740 containing one or more user-activatable controls through which the qualitative feedback may be communicated to the APS for the purpose of adjusting the controller gain and ceasing to adjust the controller gain once a satisfactory, value of controller gain has been achieved.

Figure 11:
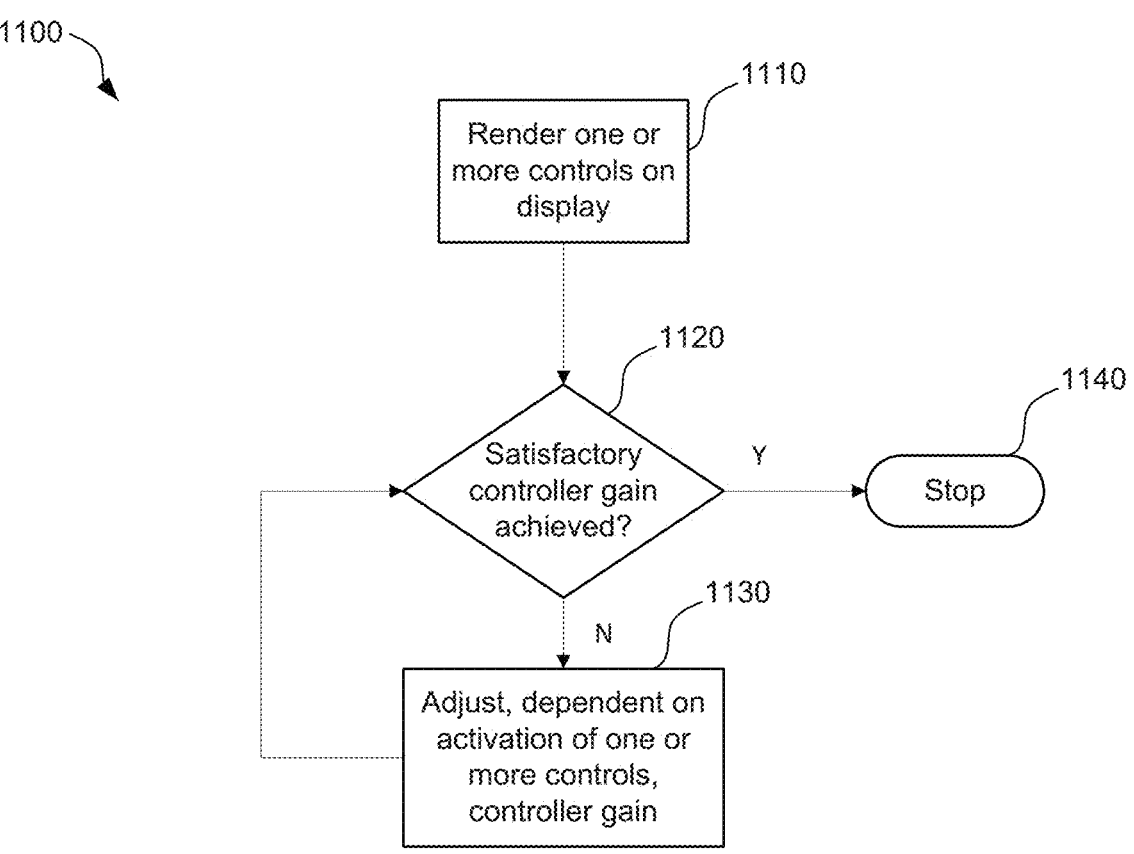
FIG. 11 is a flowchart illustrating a method of setting controller gain based on qualitative patient feedback in accordance with a further aspect of the present technology.

FIG. 11 is a flowchart illustrating a method 1100 of setting controller gain of an implantable closed-loop neuromodulation device based on qualitative patient feedback in accordance with one aspect of the present technology. The method 1100 starts at step 1110, at which one or more controls are rendered on a display of a user interface on an external computing device in communication with the implantable closed-loop neuromodulation device. Step 1120 then checks whether, based on activation of the one or more controls, a satisfactory value of the controller gain of the implantable closed-loop neuromodulation device has been achieved. If so ("Y"), the method 1100 ends at step 1140. If not, the method 1100 at step 1130 adjusts the controller gain based on activation of the one or more controls. The method 1100 then returns to step 1120.

Figures 12A, 12B, 12C, 12D:
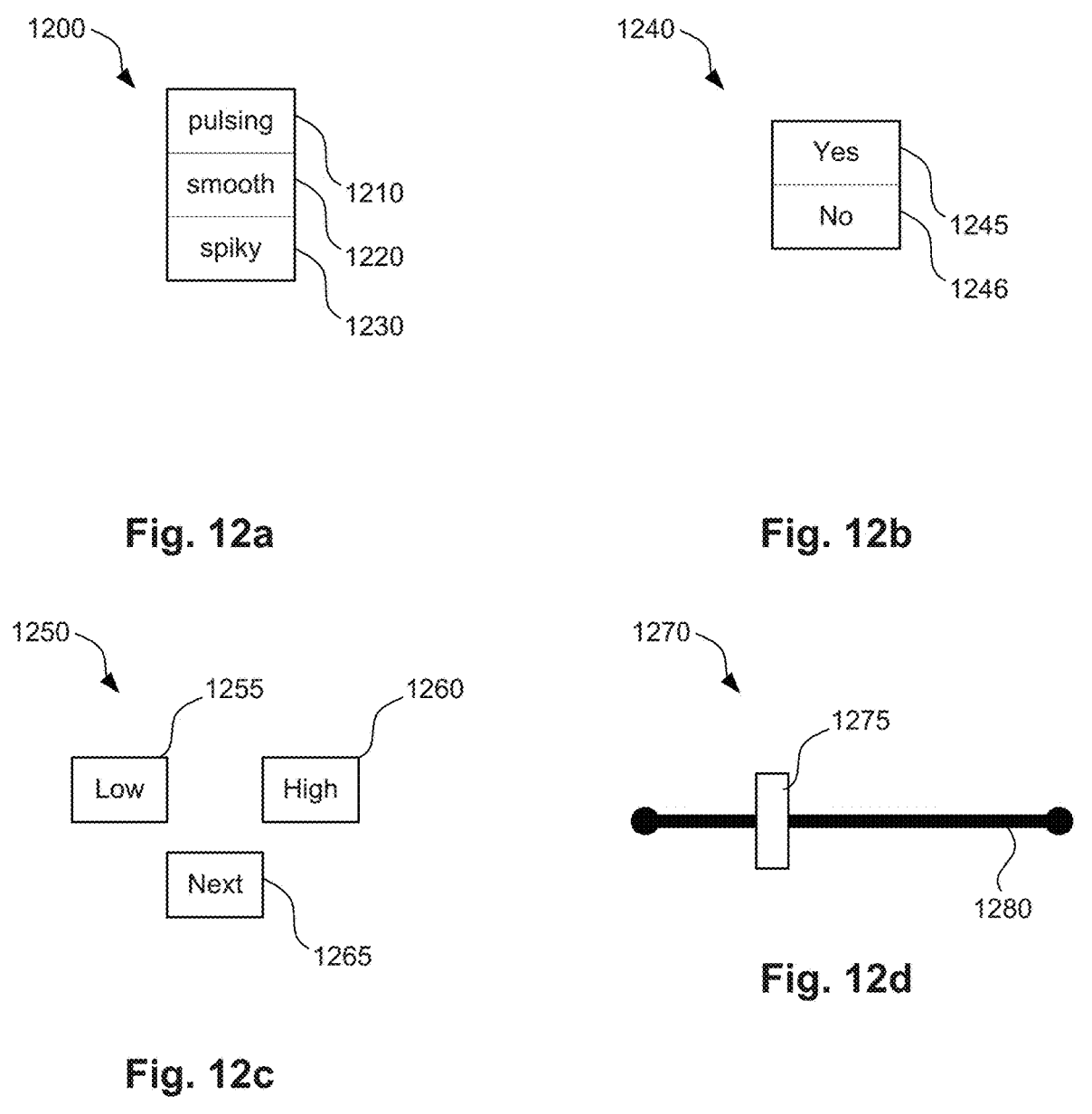

In one such implementation, the APS may provide a user interface on the CI 740 through which the patient may select from a drop-down list of qualitative descriptors of their sensation e.g. "pulsing", "spiky", and "smooth", for successive values of controller gain K. FIG. 12*a* illustrates such an interface 1200, comprising three selectable descriptors 1210 to 1230 marked as "pulsing" (1210), "smooth" (1220), and "spiky" (1230). The controller gain K may be adjusted depending on the selected descriptor. For example, if the patient selects the descriptor 1230 marked "spiky", this is taken to mean the noise amplification is unacceptably large, so K is decreased. For example, if the patient selects the descriptor 1210 marked "pulsing", this is taken to mean the posture wave amplification is unacceptably large, so K is increased. The optimal controller gain is the value of K at which patient selects the descriptor 1220 marked "smooth".

In another such implementation, the controller gain is set to alternate between two widely separated values, at one of which (for example 2) the patient should feel the sensation to be "spiky", at the other (for example 0) the patient should feel the sensation to be "pulsing". The patient is prompted to enter "Yes" or "No" by activating respective controls on the APS user interface depending on whether they can tell the difference between the two sensations. One such user interface 1240 is illustrated in FIG. 12*b*. The user interface 1240 contains two controls, one (1245) marked "Yes", and the other (1246) marked "No". Each time the patient activates one of the two controls, one or both of the controller gain values are changed. As the patient continues to enter "Yes", the two controller gain values are gradually brought closer together until the patient cannot tell the difference and enters "No". The two values of controller gain will then closely surround the optimum controller gain. A value in between the two final values of controller gain, e.g. the midpoint, may be taken as the optimal controller gain.

In another such implementation, the APS user interface presents two controls, e.g. marked "Low" and "High", representing alternative values of controller gain, on the user interface for selection by the patient. The two represented values are preferably two values at opposite ends of the expected range of controller gains (for example 0 and 2). FIG. 12*c* illustrates such a user interface 1250, comprising a control 1255 marked "Low", a control 1260 marked "High", and a control 1265 marked "Next". As each control 1255 and 1260 is selected, the corresponding value of controller gain is selected to close the loop. The patient selects the control representing their preferred value of controller gain and activates the "Next" control 1265 to confirm their selection, and another two gain values are chosen to be represented by the "Low" and "High" controls 1255 and 1260. If the patient selects the control representing the higher gain as preferable, that higher value is kept to be represented by the "High" control and the value represented by the "Low" control is brought nearer to, but still lower than, that higher value, for example as the midpoint of the interval between the original two values. This binary choice process is then repeated. Eventually, the patient's preference for higher or lower gain will flip, which means they are near their optimum controller gain. In one implementation, the method ends with the value of gain represented by the finally selected control being taken as the optimal controller gain. In another implementation, the binary choice process is repeated with the value represented by the other control being chosen on the other side of the selected value. If the patient selects the same value a second time, the value of gain represented by the selected control may be taken as the optimal controller gain with greater confidence as the patient has rejected values both higher and lower than it. This approach may be repeated multiple times to further increase confidence.

In yet another such implementation, the APS user interface presents a "slider" control to the patient. FIG. 12*d* illustrates such an interface 1270, comprising a slider control 1275 that is manipulable along the interval 1280 between two end points. The position of the slider control 1275 along the interval 1280 represents a value of controller gain between two values at opposite ends of the expected range of controller gains (for example 0 and 2). As the patient manipulates the slider control 1275 back and forth along the interval 1280, the controller gain varies between the two end values in accordance with the position of the slider control 1275 along the interval 1280. When the patient is satisfied with their sensation, the final value of the controller gain may be taken as the optimal controller gain.

In yet another such implementation, a method similar to the method 1000 is used. However, step 1020 is skipped, and the test at step 1030 is a test whether the patient has activated a control on the APS user interface representing "smooth enough". If not ("N"), the controller gain continues to be adjusted (step 1040) in the same direction. If the "smooth enough" control has been activated ("Y" at step 1030), the method ends at step 1050 with the current value of the controller gain K being taken as the optimal value $K_{opt}$ of the controller gain.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

Examples of the Invention

1. A closed-loop neuromodulation system comprising:
   a closed-loop neuromodulation device comprising a feedback controller which completes a feedback loop, the feedback controller using one or more controller parameters to control a stimulus parameter so as to maintain a measured neural response intensity at a target; and
   a processor configured to compute an optimal value of the one or more controller parameters of the feedback loop of the closed-loop neurostimulation device from a representative value of a characteristic of the feedback loop, the representative value having been derived from data of previously programmed patients.

2. The neuromodulation system of example 1, wherein the processor is further configured to measure a sensitivity of the neural tissue based on the values of the stimulus intensity parameter and the corresponding measured neural response intensities.

3. The neuromodulation system of example 2, wherein the one or more controller parameters comprises a controller gain, and the processor is configured to compute the optimal value of the controller gain using the measured sensitivity as well as the representative value of the loop characteristic.

4. The neuromodulation system of example 3, wherein the representative value of the loop characteristic is a loop gain, and the processor is configured to compute the optimal value of the controller gain by dividing the loop gain by the measured sensitivity.

5. The neuromodulation system of example 3, wherein the processor is configured to compute the optimal value of the controller gain by:
   computing an optimal value of loop gain of the feedback loop from the representative value of the loop characteristic, and
   dividing the optimal value of the loop gain by the measured sensitivity.

6. The neuromodulation system of example 1, wherein the one or more controller parameters comprises a controller gain, and the processor is configured to compute the optimal value of the controller gain by:
   measuring a value of the loop characteristic;
   adjusting the controller gain based on the measured value and the representative value of the loop characteristic; and
   repeating the measuring and adjusting until the measured value is within a predetermined distance from the representative value of the loop characteristic.

7. The neuromodulation system of example 6, wherein the processor is configured to measure the value of the loop characteristic by measuring a loop gain of the feedback loop from a response of the neural response intensity to a step change in the target.

8. The neuromodulation system of example 7, wherein the representative value of the loop characteristic is a loop gain of the feedback loop, and the measured value of the loop characteristic is the measured loop gain.

9. The neuromodulation system of example 1, further comprising an external computing device in communication with the neuromodulation device.

10. The neuromodulation system of example 9, wherein the processor forms part of the external computing device.

11. The neuromodulation system of example 1, wherein the processor forms part of the neuromodulation device.

12. A closed-loop neural stimulation system comprising:
    an implantable closed-loop neuromodulation device configured to provide neural stimuli to be delivered via the one or more stimulus electrodes to a neural pathway of a patient in order to evoke a neural response on the neural pathway, the device comprising a feedback controller which completes a feedback loop, the feedback controller using a controller gain to control a stimulus parameter so as to maintain a measured neural response intensity at a target value; and
    an external computing device in communication with the closed-loop neuromodulation device, the external computing device comprising:
    a display, and
    a processor configured to:
        render one or more controls on the display;
        adjust, dependent on activation of one of the one or more controls by a user, a value of a controller gain of the feedback loop of the closed-loop neuromodulation device.

13. The closed-loop neural stimulation system of example 12, wherein the processor is further configured to repeat the adjusting until a satisfactory controller gain is achieved.

14. The closed-loop neuromodulation system of example 13, wherein the satisfactory controller gain is the value of the controller gain upon activation of one of the one or more controls by the user.

15. The closed-loop neural stimulation system of example 12, wherein the one or more controls comprise a plurality of controls, and the processor is configured to adjust the value of the controller gain based on the control of the plurality of controls that is activated.

16. The closed-loop neural stimulation system of example 15, wherein the processor is configured not to adjust the value of the controller gain upon activation of a predetermined control of the plurality of controls by the user.

17. The closed-loop neural stimulation system of example 15, wherein the processor is further configured to:
    alternate the controller gain between two alternative values, and
    adjust at least one of the two alternative values upon activation of a predetermined control of the plurality of controls by the user.

18. The closed-loop neural stimulation system of example 17, wherein the processor is configured to adjust the value of the controller gain to a value in between the two alternative values upon activation of another predetermined control of the plurality of controls by the user.

19. The closed-loop neural stimulation system of example 15, wherein the processor is further configured to alternate the controller gain between two alternative values upon activation of either of two respective controls of the plurality of controls.

20. The closed-loop neural stimulation system of example 19, wherein the processor is further configured to adjust at least one of the two alternative values upon activation of a predetermined control of the plurality of controls by the user.

21. An automated method of controlling a closed-loop neuromodulation device to deliver a neural stimulus to a patient using an external computing device in communication with the neuromodulation device, the method comprising:

rendering, by a processor of the external computing device, one or more controls on a display of the external computing device; and adjusting, dependent on activation of one of the one or more controls by a user, a value of a controller gain of the feedback loop of the closed-loop neuromodulation device.

22. The method of example 21, further comprising repeating the adjusting until a satisfactory controller gain is achieved.

23. The method of example 22, wherein the satisfactory controller gain is the value of the controller gain upon activation of one of the one or more controls by the user.

24. The method of example 21, wherein the one or more controls comprise a plurality of controls, and the adjusting comprises adjusting the value of the controller gain based on the control of the plurality of controls that is activated.

25. The method of example 24, further comprising not adjusting the value of the controller gain upon activation of a predetermined control of the plurality of controls by the user.

26. The method of example 24, further comprising:

alternating the controller gain between two alternative values, and adjusting at least one of the two alternative values upon activation of a predetermined control of the plurality of controls by the user.

27. The method of example 26, further comprising adjusting the value of the controller gain to a value in between the two alternative values of the controller gain upon activation of another predetermined control of the plurality of controls by the user.

28. The method of example 24, further comprising alternating the controller gain between two alternative values upon activation of either of two respective controls of the plurality of controls.

29. The method of example 28, wherein further comprising adjusting at least one of the two alternative values upon activation of a predetermined control of the plurality of controls by the user.

| LABEL LIST | |
| --- | --- |
| implanted stimulator | 100 |
| patient | 108 |
| electronics module | 110 |
| battery | 112 |
| telemetry module | 114 |
| controller | 116 |
| memory | 118 |
| clinical data | 120 |
| clinical settings | 121 |
| control programs | 122 |
| pulse generator | 124 |
| electrode selection module | 126 |
| measurement circuitry | 128 |
| ground | 130 |
| electrode array | 150 |

-continued

| LABEL LIST | |
| --- | --- |
| biphasic stimulus pulse | 160 |
| neural response | 170 |
| nerve | 180 |
| communications channel | 190 |
| external computing device | 192 |
| CLNS system | 300 |
| clinical settings controller | 302 |
| target ECAP controller | 304 |
| box | 308 |
| box | 309 |
| feedback controller | 310 |
| box | 311 |
| stimulator | 312 |
| element | 313 |
| measurement circuitry | 318 |
| detector | 320 |
| comparator | 324 |
| gain element | 336 |
| integrator | 338 |
| activation plot | 402 |
| ECAP threshold | 404 |
| discomfort threshold | 408 |
| perception threshold | 410 |
| therapeutic range | 412 |
| activation plot | 502 |
| activation plot | 504 |
| activation plot | 506 |
| ECAP threshold | 508 |
| ECAP threshold | 510 |
| ECAP threshold | 512 |
| ECAP target | 520 |
| ECAP | 600 |
| neuromodulation system | 700 |
| device | 710 |
| remote controller | 720 |
| clinical settings transceiver | 730 |
| clinical interface | 740 |
| charger | 750 |
| discrete - time CLNS system | 800 |
| element | 820 |
| delay element | 837 |
| element | 838 |
| delay element | 850 |
| method | 900 |
| step | 910 |
| step | 920 |
| method | 1000 |
| step | 1010 |
| step | 1020 |
| step | 1030 |
| step | 1040 |
| step | 1050 |
| method | 1100 |
| step | 1110 |
| step | 1120 |
| step | 1130 |
| step | 1140 |
| user interface | 1200 |
| control | 1210 |
| control | 1220 |
| control | 1230 |
| user interface | 1240 |
| control | 1245 |
| control | 1246 |
| user interface | 1250 |
| control | 1255 |
| control | 1260 |
| control | 1265 |
| user interface | 1270 |
| control | 1275 |
| interval | 1280 |

The invention claimed is:

1. A neuromodulation system comprising:

a neuromodulation device for controllably delivering a neural stimulus, the neuromodulation device comprising:

a plurality of implantable electrodes including one or more stimulus electrodes and one or more sense electrodes;

a stimulus source configured to provide a neural stimulus to be delivered via the one or more stimulus electrodes to a neural pathway of a patient in order to evoke a neural response on the neural pathway;

measurement circuitry configured to process a signal sensed at the one or more sense electrodes subsequent to the delivered neural stimulus, the sensed signal including an evoked neural response; and a control unit configured to:

control the stimulus source to provide the neural stimulus according to a stimulus intensity parameter;

measure an intensity of the evoked neural response in the sensed signal; and implement a feedback controller which completes a feedback loop, the feedback controller configured to complete the feedback loop by using the measured intensity and one or more controller parameters to adjust the stimulus intensity parameter so as to maintain the measured intensity at a target value; and a processor configured to:

determine optimal values of the one or more controller parameters from a predetermined representative value of a variable that characterises performance of the feedback loop, the predetermined representative value having been derived from data of previously programmed patients.

2. The neuromodulation system of claim 1, wherein the processor is further configured to measure a sensitivity of the neural pathway based on the values of the stimulus intensity parameter and the corresponding measured neural response intensities.

3. The neuromodulation system of claim 2, wherein the one or more controller parameters comprises a controller gain, and the processor is configured to determine the optimal value of the controller gain using the measured sensitivity as well as the predetermined representative value of the variable.

4. The neuromodulation system of claim 3, wherein the variable is a loop gain, and the processor is configured to determine the optimal value of the controller gain by dividing the predetermined representative value of the loop gain by the measured sensitivity.

5. The neuromodulation system of claim 3, wherein the processor is configured to determine the optimal value of the controller gain by:

determining an optimal value of loop gain of the feedback loop from the predetermined representative value of the variable, and dividing the optimal value of the loop gain by the measured sensitivity.

6. The neuromodulation system of claim 5, wherein the predetermined representative value of the variable is a cutoff frequency of the feedback loop.

7. The neuromodulation system of claim 5, wherein the predetermined representative value of the variable is a time constant of the feedback loop.

8. The neuromodulation system of claim 5, wherein the predetermined representative value of the variable is a noise amplification ratio of the feedback loop.

9. The neuromodulation system of claim 5, wherein the predetermined representative value of the variable is a posture wave amplification ratio of the feedback loop.

10. The neuromodulation system of claim 5, wherein the predetermined representative value of the variable is a total amplification of the feedback loop, the total amplification comprising a noise amplification ratio of the feedback loop and a posture wave amplification ratio of the feedback loop.

11. The neuromodulation system of claim 9, further comprising an external sensor configured to measure a frequency of the posture wave.

12. The neuromodulation system of claim 1, wherein one or more controller parameters comprises a controller gain, and the processor is configured to determine the optimal value of the controller gain by:

determining a value of the variable that characterises performance of the feedback loop;

adjusting the controller gain based on the determined value and the predetermined representative value of the variable; and repeating the determining and adjusting until the determined value of the variable is within a predetermined distance from the predetermined representative value of the variable.

13. The neuromodulation system of claim 12, wherein the processor is configured to determine the value of the variable by measuring a loop gain of the feedback loop from a response of the neural response intensity to a step change in the target value.

14. The neuromodulation system of claim 13, wherein the predetermined representative value of the variable is a loop gain of the feedback loop, and the determined value of the variable is the measured loop gain.

15. The neuromodulation system of claim 13, wherein the predetermined representative value of the variable is a cutoff frequency of the feedback loop, and the processor is configured to determine the value of the variable from the measured loop gain.

16. The neuromodulation system of claim 13, wherein the predetermined representative value of the variable is a time constant of the feedback loop, and the processor is configured to determine the value of the variable from the measured loop gain.

17. The neuromodulation system of claim 13, wherein the predetermined representative value of the variable is a noise amplification ratio of the feedback loop, and the processor is configured to determine the value of the variable from the measured loop gain.

18. The neuromodulation system of claim 13, wherein the predetermined representative value of the variable is a posture wave amplification ratio of the feedback loop, and the processor is configured to determine the value of the variable from the measured loop gain.

19. The neuromodulation system of claim 13, wherein the predetermined representative value of the variable is a total amplification of the feedback loop, the total amplification comprising a noise amplification ratio of the feedback loop and a posture wave amplification ratio of the feedback loop, and the processor is configured to determine the value of the variable from the measured loop gain.

20. The neuromodulation system of claim 18, further comprising an external sensor configured to measure a frequency of the posture wave.

21. The neuromodulation system of claim 1, further comprising an external computing device in communication with the neuromodulation device.

22. The neuromodulation system of claim 21, wherein the processor forms part of the external computing device.

23. The neuromodulation system of claim 1, wherein the processor forms part of the neuromodulation device.

24. An automated method of controlling a neuromodulation device to deliver a neural stimulus to neural tissue of a patient, the method comprising:

delivering the neural stimulus to the neural tissue according to a value of a stimulus intensity parameter;

measuring an intensity of a neural response evoked by the stimulus, completing a feedback loop by using the measured intensity and one or more controller parameters to adjust the stimulus intensity parameter so as to maintain the measured intensity at a target value; and determining optimal values of the one or more controller parameters from a predetermined representative value of a variable that characterises performance of the feedback loop, the predetermined representative value having been derived from data of previously programmed patients.

25. The method of claim 24, further comprising measuring a sensitivity of the neural tissue based on the values of the stimulus intensity parameter and the corresponding measured neural response intensities.

26. The method of claim 25, wherein the one or more controller parameters comprises a controller gain, and determining the optimal value of the controller gain uses the measured sensitivity as well as the predetermined representative value of the variable.

27. The method of claim 24, wherein the one or more controller parameters comprises a controller gain, and determining the optimal value of the controller gain comprises:

measuring a value of the variable;

adjusting the controller gain based on the measured value and the predetermined representative value of the variable; and repeating the measuring and adjusting until the measured value of the variable is within a predetermined distance from the predetermined representative value of the variable.

28. The method of claim 27, wherein measuring the value of the variable comprises measuring a loop gain of the feedback loop from a response of the neural response intensity to a step change in the target value.

29. A neural stimulation system comprising:

a neuromodulation device for controllably delivering a neural stimulus, the neuromodulation device comprising:

a plurality of implantable electrodes including one or more stimulus electrodes and one or more sense electrodes;

a stimulus source configured to provide a neural stimulus to be delivered via the one or more stimulus electrodes to a neural pathway of a patient in order to evoke a neural response on the neural pathway;

measurement circuitry configured to process a signal sensed at the one or more sense electrodes subsequent to the delivered neural stimulus, the sensed signal including an evoked neural response; and a control unit configured to:

control the stimulus source to provide the neural stimulus according to a stimulus intensity parameter;

measure an intensity of the evoked neural response in the sensed signal; and implement a feedback controller which completes a feedback loop, the feedback controller configured to complete the feedback loop by using the measured intensity and one or more controller parameters to adjust the stimulus intensity parameter so as to maintain the measured intensity at a target value; and a processor configured to:

determine optimal values of the one or more controller parameters from a predetermined value of an amplification parameter of the feedback loop.

30. The neural stimulation system of claim 29, wherein the processor is further configured to measure a sensitivity of the neural pathway based on the values of the stimulus intensity parameter and the corresponding measured neural response intensities.

31. The neural stimulation system of claim 30, wherein the one or more controller parameters comprises a controller gain, and the processor is configured to determine the optimal value of the controller gain using the measured sensitivity as well as the predetermined value of the amplification parameter of the feedback loop.

32. The neural stimulation system of claim 31, wherein the processor is configured to determine the optimal value of the controller gain by:

determining an optimal value of loop gain of the feedback loop from the predetermined value, and dividing the optimal value of the loop gain by the measured sensitivity.

33. The neural stimulation system of claim 32, wherein predetermined value is a noise amplification ratio of the feedback loop.

34. The neural stimulation system of claim 32, wherein the predetermined value is a posture wave amplification ratio of the feedback loop.

35. The neural stimulation system of claim 32, wherein the predetermined value is a total amplification of the feedback loop, the total amplification comprising a noise amplification ratio of the feedback loop and a posture wave amplification ratio of the feedback loop.

36. The neural stimulation system of claim 34, further comprising an external sensor configured to measure a frequency of the posture wave.

37. The neural stimulation system of claim 29, wherein the one or more controller parameters comprises a controller gain, and the processor is configured to determine the optimal value of the controller gain by:

determining a value of the amplification parameter;

adjusting the controller gain based on the determined value and the predetermined value of the amplification parameter; and repeating the determining and adjusting until the determined value of the amplification parameter is within a predetermined distance from the predetermined value of the amplification parameter.

38. The neural stimulation system of claim 37, wherein the processor is configured to determine the value of the amplification parameter by measuring a loop gain of the feedback loop from a response of the neural response intensity to a step change in the target value.

39. The neural stimulation system of claim 38, wherein the predetermined value of the amplification parameter is a noise amplification ratio of the feedback loop, and the processor is configured to determine the value of the amplification parameter from the measured loop gain.

40. The neural stimulation system of claim 38, wherein the predetermined value of the amplification parameter is a posture wave amplification ratio of the feedback loop, and the processor is configured to determine the value of the amplification parameter from the measured loop gain.

41. The neural stimulation system of claim 38, wherein the predetermined value of the amplification parameter is a total amplification of the feedback loop, the total amplification comprising a noise amplification ratio of the feedback loop and a posture wave amplification ratio of the feedback loop, and the processor is configured to determine the value of the amplification parameter from the measured loop gain.

42. The neural stimulation system of claim 40, further comprising an external sensor configured to measure a frequency of the posture wave.

43. The neural stimulation system of claim 29, further comprising an external computing device in communication with the neuromodulation device.

44. The neural stimulation system of claim 43, wherein the processor forms part of the external computing device.

45. The neural stimulation system of claim 29, wherein the processor forms part of the neuromodulation device.

46. An automated method of controlling a neuromodulation device to deliver a neural stimulus to neural tissue of a patient, the method comprising:

delivering the neural stimulus to the neural tissue according to a stimulus intensity parameter;

measuring an intensity of a neural response evoked by the stimulus, completing a feedback loop by using the measured intensity and one or more controller parameters to adjust the stimulus intensity parameter so as to maintain the measured intensity at a target value; and determining optimal values of the one or more controller parameters from a predetermined value of an amplification parameter of the feedback loop.

47. The method of claim 46, further comprising measuring a sensitivity of the neural tissue based on the values of the stimulus intensity parameter and the corresponding measured neural response intensities.

48. The method of claim 47, wherein the one or more controller parameters comprises a controller gain, and the determining the optimal value of the controller gain comprises using the measured sensitivity as well as the predetermined value of the amplification parameter of the feedback loop.

49. The method of claim 48, wherein the determining the optimal value of the controller gain comprises:

determining an optimal value of loop gain of the feedback loop from the predetermined value, and dividing the optimal value of the loop gain by the measured sensitivity.

50. The method of claim 49, wherein predetermined value is a noise amplification ratio of the feedback loop.

51. The method of claim 49, wherein the predetermined value is a posture wave amplification ratio of the feedback loop.

52. The method of claim 49, wherein the predetermined value is a total amplification of the feedback loop, the total amplification comprising a noise amplification ratio of the feedback loop and a posture wave amplification ratio of the feedback loop.

53. The method of claim 51, further comprising an external sensor configured to measure a frequency of the posture wave.

54. The method of claim 46, wherein the one or more controller parameters comprises a controller gain, and the determining the optimal value of the controller gain comprises:

determining a value of the amplification parameter;

adjusting the controller gain based on the determined value and the predetermined value of the amplification parameter; and repeating the measuring and adjusting until the determined value of the amplification parameter is within a predetermined distance from the predetermined value of the amplification parameter.

55. The method of claim 54, wherein the determining the value of the amplification parameter comprises measuring a loop gain of the feedback loop from a response of the neural response intensity to a step change in the target value.

56. The method of claim 55, wherein the predetermined value of the amplification parameter is a noise amplification ratio of the feedback loop, and the determining the value of the amplification parameter uses the measured loop gain.

57. The method of claim 55, wherein the predetermined value of the amplification parameter is a posture wave amplification ratio of the feedback loop, and the determining the value of the amplification parameter uses the measured loop gain.

58. The method of claim 55, wherein the predetermined value of the amplification parameter is a total amplification of the feedback loop, the total amplification comprising a noise amplification ratio of the feedback loop and a posture wave amplification ratio of the feedback loop, and the determining the measured value of the amplification parameter uses the measured loop gain.

59. The method of claim 57, further comprising an external sensor configured to measure a frequency of the posture wave.

\* \* \* \* \*